US007297657B2

(12) United States Patent
Morgenstern

(10) Patent No.: US 7,297,657 B2
(45) Date of Patent: Nov. 20, 2007

(54) PROCESS FOR THE PREPARATION OF N-(PHOSPHONOMETHYL)GLYCINE BY OXIDIZING N-SUBSTITUTED N-(PHOSPHONOMETHYL)GLYCINE

(75) Inventor: David A. Morgenstern, Creve Coeur, MO (US)

(73) Assignee: Monsanto Technology LLC, St. Louis, MO (US)

( * ) Notice: Subject to any disclaimer, the term of this patent is extended or adjusted under 35 U.S.C. 154(b) by 351 days.

(21) Appl. No.: 10/441,454

(22) Filed: May 20, 2003

(65) Prior Publication Data

US 2004/0143134 A1    Jul. 22, 2004

Related U.S. Application Data

(60) Division of application No. 09/776,801, filed on Feb. 5, 2001, now abandoned, which is a division of application No. 09/263,171, filed on Mar. 5, 1999, now Pat. No. 6,232,494, which is a continuation-in-part of application No. 09/023,404, filed on Feb. 12, 1998, now Pat. No. 6,005,140.

(60) Provisional application No. 60/096,207, filed on Aug. 12, 1998.

(51) Int. Cl.
*B01J 23/72* (2006.01)

(52) U.S. Cl. ......................... 502/345; 562/17

(58) Field of Classification Search ................. 502/314
See application file for complete search history.

(56) References Cited

U.S. PATENT DOCUMENTS

| 3,330,749 A | 7/1967 | Kuwata et al. |
| 3,340,097 A | 9/1967 | Hess et al. |
| 3,583,972 A | 6/1971 | Birkenmeyer et al. |
| 3,799,758 A | 3/1974 | Franz |
| 3,835,000 A | 9/1974 | Frazier et al. |
| 3,927,080 A | 12/1975 | Gaeiner |
| 3,950,402 A | 4/1976 | Franz |
| 3,954,848 A | 5/1976 | Franz |
| 3,956,370 A | 5/1976 | Parry et al. |
| 3,969,398 A | 7/1976 | Hershman |
| 4,026,950 A | 5/1977 | Le Ludec |
| 4,097,533 A | 6/1978 | Scheben |
| 4,119,430 A | 10/1978 | Gaertner et al. |
| 4,131,448 A | 12/1978 | Franz |
| 4,147,719 A | 4/1979 | Franz |
| 4,190,605 A | 2/1980 | Muench et al. |
| 4,264,776 A | 4/1981 | Hershman et al. |
| 4,507,250 A | 3/1985 | Bakel |
| 4,525,294 A | 6/1985 | Sartori et al. |
| 4,582,650 A | 4/1986 | Felthouse |
| 4,624,937 A | 11/1986 | Chou |
| 4,654,429 A | 3/1987 | Balthazor et al. |
| 4,696,772 A | 9/1987 | Chou |
| 4,775,498 A | 10/1988 | Gentilcore |
| 4,810,426 A | 3/1989 | Fields, Jr. et al. |
| 4,847,013 A | 7/1989 | Müller |
| 4,851,131 A | 7/1989 | Grabiak et al. |
| 4,921,991 A | 5/1990 | Lacroix |
| 4,978,649 A | 12/1990 | Surovikin et al. |
| 5,068,404 A | 11/1991 | Miller et al. |
| 5,087,740 A | 2/1992 | Smith |
| 5,179,228 A | 1/1993 | Martin Ramon et al. |
| 5,292,936 A | 3/1994 | Franczyk |
| 5,356,849 A | 10/1994 | Matviya et al. |

(Continued)

FOREIGN PATENT DOCUMENTS

| DE | 336153 | 4/1921 |
| EP | 0 055 695 | 7/1982 |
| EP | 0 408 528 A1 | 1/1991 |
| EP | 0 472 693 A1 | 3/1992 |
| EP | 0 680 948 A1 | 7/1997 |

(Continued)

OTHER PUBLICATIONS

Kallen, R.G., Equilibria for the Reaction of Cysteine and Derivatives with Formaldehyde and Protons, *Journal of the American Chemical Society*, Nov. 17, 1971, pp. 6227-6235, vol. 93, No. 23.

(Continued)

*Primary Examiner*—Kamal A. Saeed
(74) *Attorney, Agent, or Firm*—Senniger Powers; Joseph A. Schaper

(57) ABSTRACT

This invention is directed to an improved process for the preparation of N-(phosphonomethyl)glycine (i.e., "glyphosate"), a salt of N-(phosphonomethyl)glycine, or an ester of N-(phosphonomethyl)glycine. The process comprises combining an N-substituted N-(phosphonomethyl)glycine reactant with oxygen in the presence of a noble metal catalyst. The N-substituted N-(phosphonomethyl)glycine reactant has formula (V):

$$R^7O-\overset{O}{\underset{\|}{C}}-CH_2-N-CH_2-\overset{O}{\underset{\|}{P}}\overset{OR^8}{\diagdown OR^9}, \quad (V)$$
$$\phantom{R^7O-C-CH_2-N}\overset{|}{R^1-\underset{|}{C}-H}$$
$$\phantom{R^7O-C-CH_2-N-}R^2$$

wherein $R^1$ and $R^2$ are independently selected from the group consisting of hydrogen, halogen, $-PO_3R^{12}R^{13}$, $-SO_3R^{14}$, $-NO_2$, hydrocarbyl, and substituted hydrocarbyl other than $-CO_2R^{15}$; and $R^7$, $R^8$, $R^9$, $R^{12}$, $R^{13}$, $R^{14}$ and $R^{15}$ are independently selected from the group consisting of hydrogen, hydrocarbyl, substituted hydrocarbyl, and an agronomically acceptable cation.

50 Claims, 1 Drawing Sheet

U.S. PATENT DOCUMENTS

| | | | |
|---|---|---|---|
| 5,367,112 | A | 11/1994 | Franczyk |
| 5,500,485 | A | 3/1996 | Hodgkinson |
| 5,585,083 | A | 12/1996 | Kielin et al. |
| 5,602,276 | A | 2/1997 | Stern et al. |
| 5,606,107 | A | 2/1997 | Smith |
| 5,627,125 | A | 5/1997 | Ebner et al. |
| 5,658,839 | A | 8/1997 | de Agudelo et al. |
| 5,683,829 | A | 11/1997 | Sarangapani |
| 5,688,994 | A | 11/1997 | Baysdon et al. |
| 5,703,273 | A | 12/1997 | Stern et al. |
| 6,005,140 | A | 12/1999 | Morgenstern et al. |
| 6,417,133 | B1 * | 7/2002 | Ebner et al. ............. 502/185 |

FOREIGN PATENT DOCUMENTS

| | | |
|---|---|---|
| EP | 0 858 835 | 8/1998 |
| GB | 1 366 591 | 9/1974 |
| GB | 1 388 400 | 3/1975 |
| GB | 1 436 844 | 5/1976 |
| GB | 1 449 875 | 9/1976 |
| GB | 2 001 074 A | 1/1979 |
| GB | 1 575 949 | 10/1980 |
| JP | 95-141575 | 12/1996 |
| WO | WO95/00523 A1 | 3/1996 |
| WO | WO99/41360 A1 | 8/1999 |

OTHER PUBLICATIONS

Moedritzer, K., et al., The Direct Synthesis of α-Aminothylphosphonic Acids, Mannich-Type Reactions with Orthophosphorous Acid, *Journal of Organic Chemistry*, May 1966, pp. 1603-1607.

Nielson, A.T., et al., Polyazapolycyclics by Condensation of Aldehydes with Amines. 3. Formation of 2,4,6,8-tetraazabicyclo[3.3.0]octanes from Formaldehyde, Glyoxal, and Benzylamines, *Journal of Organic Chemistry*, 1992, pp. 6756-6759, vol. 57, No. 25, American Chemical Society.

Rajan, K.S., et al., Ethylenediamine-N,N '-diacetic-N,N'-di (methylenephosphonic) Acid, *Journal of the American Chemical Society*, Jul. 30, 1969, pp. 4408-4412, vol. 91, No. 16.

Riley, D.P., et al., Electron-Transfer Agents in Metal-Catalyzed Dioxygen Oxidations: Effective Catalysts for the Interception and Oxidation of Carbon Radicals, *Journal of the American Chemical Society*, 1992, pp. 1881-1882, vol. 114.

Wallace, E.M., et al., Design and Synthesis of Potent, Selective Inhibitors of Endothelin-Converting Enzyme, *Journal of Medicinal Chemistry*, Apr. 8, 1998, pp. 1513-1523, vol. 41, No. 9, American Chemical Society.

Westerback, S., et al., Amino Acids Containing Methylenephosphonate Groups, *Journal of the American Chemical Society*, Jun. 20, 1965, pp. 2567-2572, vol. 87, No. 12.

Alagi, D., et al., Well-defined Redox-Active Polymers and Block Copolymers Prepared by Living Ring-Opening Metathesis Polymerization, *Journal of the American Society*, 1992, pp. 4150-4158.

Andrew, M.R., et al., The Characterization of PVSn Catalyst for the Electrochemical Oxidation of Methanol, *Journal of Applied Electrochemistry*, 1976, pp. 99-106, vol. 6.

Arico, A.S., et al., Methanol Oxidation on Carbon-Supported Pt-Sn Electrodes in Silicolungstic Acid, *Electrochemical Acta*, 1994, pp. 691-700, vol. 39, No. 5.

Balakrishnon, K., et al., A Chemisorption and XPS Study of Bimetallic Pt-Sn/Al$_2$O$_3$ Catalysts, *Journal of Catalysts*, 1991, pp. 287-306.

Bettermann, G., et al., Phosphorus Compounds, Inorganic, *Ullmann's Encyclopedia of Industrial Chemistry*, 1991, pp. 527-543, vol. A19.

Burch, R., The Oxidation State of Tine and the Interaction Between Platinum and Tin, *Journal of Catalysts*, 1981, pp. 348-359.

Cameron, D.S., et al., Carbons as Supports for Precious Metal Catalysts, *Catalysis Today*, 1990, pp. 113-137, vol. 7.

Campbell, S., et al., Effect of Bi and Sn Adatoms on Formic Acid and Methanol Oxidation at Well Defined Plantinum Surfaces, *Journal of Chemical Society*, Faraday Trans., 1992, pp. 833-841, vol. 88, No. 6.

Cathro, K.J., The Oxidation of Water-Soluble Organic Fuels Using Platinum-Tin Catalysts, *J. Electrochem. Soc.: Electrochemical Technology*, 1969, pp. 1608-1611, vol. 116, No. 11.

Coloma, F., et al., Heat-Treated Carbon Blacks as Supports for Plantinum Catalysts, *Journal of Catalysis*, 1995, pp. 299-305.

Coloma, F., et al., Preparation of Plantinum Supported on Pregraphitized Carbon Blacks, *Langmuir*, 1994, pp. 750-755.

Cope, A.C., et al., Synthesis of 2-Alkylaminoethanols from Ethanolamine, *Journal of the American Chemical Society*, 1942, pp. 1503-1506, vol. 64.

Dapperheld, S., et al., Substituted Triarylamine Cation-Radical Redox Systems —Synthesis, Electrochemical and Spectroscopic Properties, Hammet Behavior, and Suitability as Redox Catalysts, *Chem. Ber.*, 1991, pp. 2557-2567.

Davis, G.T., et al., Oxidation of Amines VI. Platinum-Catalyzed Air Oxidations of N-Methyl Tertiary Amines, *Tetrahedron Letters No. 38*, 1968, pp. 4085-4086.

Dubinin, M.M., Microporous Structures of Carbonaceous Absorbents, *Carbon*, 1982, pp. 195-200, vol. 20, No. 3.

Dolphin, D., et al., Polyhaloporphyrins: Unusual Ligands for Metals and Metal-Catalyzed Oxidations, *Acc. Chem. Res.*, 1997, pp. 251-259.

Dyker, G., Amino Acid Derivatives by Multicomponent Reactions, *Angew. Chem. Int. Ed. Engl.*, 1997, pp. 1700-1702, vol. 36, No. 16.

Franklin, T., et al., The Effect of Anionic Poisons on the Catalytic Oxidation of Formaldehyde on Platinum, *Journal of Catalysis*, 1976, pp. 360-366.

Franz, J.E., et al., Methods of Preparing Glyphosate, *Glyphostate: A Unique Global Herbicide*, 1997, pp. 233-262.

Fuhrnop, J-H., Reversible Reactions of Porphyrins and Metalloporphyrins and Electrochemistry, *Porphyrins and Metalloporphyrins*, 1975, pp. 593-622.

Gallezot, P., et al., Catalytic Oxidation with Air for Clean and Selective Transformations of Polyols, *Catalysis of Organic Reactions*, pp. 331-340, (Scaros, et al., eds. Marcel Dekker, Inc., New York, NY, 1994).

Gokagac, G., et al., Characterization of Carbon-Supported Pt-Sn Bimetallic Catalysts for the Electrochemical Oxidation of Methanol, *Journal of Chemical Society*, Faraday Trans., 1993, pp. 151-157, vol. 89, No. 1.

Gregor, H.P., Electrodialysis and Electro-Osmosis, *Encyclopedia of Chemical Processing and Design*, 1983, pp. 349-363 (J.J. McKetta & W.A. Cunninghams, eds., Marcel Dekker, New York, NY).

Kim, T.K. et al., Preparation of Carbon-Supported Platinum Catalysts: Absorption Mechanism of Anionic Platinum Precursor onto Carbon Support, *Carbon*, 1992, pp. 467-475, vol. 30, No. 3.

Kimura, H., et al., Palladium Based Multi-Component Catalytic Systems for the Alcohol to Carboxylate Oxidation Reaction, *Applied Catalysis A: General*, 1993, pp. 143-169, vol. 95.

Kimura, H., Selective Oxidation *of Glycerol on a Plantinumbismuth Catalyst by Using a Fixed Bed Reactor, Applied* Catalysis A: General, 1993, pp. 147-158, vol. 105.

Koene, B.E., et al., Asymmetric Triaryldiamines as Thermally Stable Hole Transporting Layers for Organic Light-Emitting Devices, *Chem. Meter.*, 1998, pp. 2235-2250, vol. 10.

Knifton, J.F., Amidocarbonylation, *Applied Homogeneous Catalysis With Organometallic Compounds*, vol. I: Applications, 1996, pp. 159-168.

Luk'Yanova, Z.V., et al., Determination of the Surface Area of Platinum in Absorption Catalysts from the Amount of 'Soluble' Platinum, *Russian Journal of Physical Chemistry*, 1979, pp. 225-227, vol. 53, No. 2.

Maier, L., Organic Phosphorus Compounds 95. A Simple Method for the Preparation of N-Dihydroxyphosphonylmethyl-Glycine (Glyphosate), *Phosphorus, Sulfur, and Silicon*, 1991, pp. 65-67, vol. 61.

Mallat, T., et al., Preparation of Promoted Platinum Catalysts of Designed Geometry and the Role of Promoters in the Liquid-Phase Oxidation of 1-Methoxy-2-Propanol, *Journal of Catalysis*, 1993, pp. 237-253.

Masui, M., et al., N-Hydroxyphtalimide as an Effective Mediator for the Oxidation of Alcohols by Electrolysis, *J. Chem. Soc. Chem. Commun.*, 1983, pp. 479-480.

Mastalerz, P., α-Substituted Phosphonates, *Handbook of Organophosphorous Chemistry*, 1992, pp. 277-371 (Robert Engel, ed., Marcel Dekker, New York, NY).

Merlen, E., et al., Characterization of Bimetallic Pt-Sn/$Al_2O_3$ Catalysts: Relationship Between Particle Size and Structure, *Journal of Catalysts 159*, 1996, pp. 178-188.

Moss, R.L., Preparation and Characterization of Supported Metal Catalysts, *Experimental Methods in Catalytic Research*, 1976, pp. 43-95, vol. II, (Robert B. Anderson, ed., Academic Press, New York, NY).

Perichon, J., Miscellaneous Hydrocarbons, *Encyclopedia of Electrochemistry of the Elements*, 1978, pp. 163-166 (Allen J. Bard & Henning Lund, eds., Marcel Dekker, New York, NY).

Prado-Burguette, C., et al., Effect of Carbon Support and Mean Pt Particle Size on Hydrogen Chemisorption by Carbon-Supported Pt Catalysts, *Journal of Catalysis 128*, 1991, pp. 397-404.

Prado-Burguette, C., et al., The Effect of Oxygen Surface Groups of the Support on Platinum Dispersion in Pt/Carbon Catalysts, *Journal of Catalysis 115*, 1989, pp. 98-106.

Redmore, D., The Chemistry of P-C-N Systems, *Topics in Phosphorus Chemistry*, 1976, pp. 515-585, vol. 8, (E.J. Griffith & M. Grayson, eds., John Wiley & Sons).

Riley, D., et al., Vanadium (IV,V) Salts as Homogeneous Catalysts for the Oxygen Oxidation of N-(Phosphonomethyl)lminodiacetic Acid to N-(Phosphonomethyl)Glycine, *Inorg., Chem.*, 1991, pp. 4191-4197, vol. 30.

Riley, D., et al., Homogeneous Catalysts for Selective Molecular Oxygen Driven Oxidative Decarbonoxylations, *Journal of the American Chemical Society*, 1991, pp. 3371-3378, vol. 113.

Rodriguez-Reinoso, F., et al., Platinum Catalysts Supported on Activitated Carbons, *Journal of Catalysis 99*, 1986, pp. 171-183.

Scott, K., *Handbook on Industrial Membranes*, 1995, Elsevier, New York.

Semmelhack, M.F., et al., Nitroxyl-Mediated Electrooxidation of Alcohols to Aldehydes and Ketones, *Journal of the American Chemical Society*, 1983, pp. 4492-4494.

Semmens, M.J., et al., Gas Transfer Without Bubbles, 1994, pp. 51-58, Fed. vol. 187, *Aeration Technology*, Book No. G00865 (R.E.A. Arndt & A. Prosperetti, eds.).

Shekhobalova, V.I., Effect of Small Additions of Kl on the Properties of Pt Absorption Catalysts, *Russian Journal of Physical Chemistry*, 1984, pp. 1759-1760, vol. 58, No. 11.

Shekhobalova, V.I., et al., Deactivation Mechanism of Platinum Catalysts During the Liquid-Phase Decomposition of Hydrogen Peroxide, *Russian Journal of Physical Chemistry*, 1979, pp. 1308-1309, vol. 53, No. 9.

Shekhobalova, V.I., et al., Relationship Between the Shape of the Kinetic Curves for the Catalytic Decomposition of Hydrogen Peroxide and the Amount of 'Soluble' Metal in the Catalyst, *Russian Journal of Physical Chemistry*, 1979, pp. 917-918, vol. 53, No. 6.

Stiles, A.B., Getting the Catalyst and the Support Together, *Catalyst Supports and Supported Catalysts, Theoretical and Applied Concepts*, 1987, pp. 1-137, Buttenworths, Boston.

Torii, S., et al., Carboxylic Acids, *Organic Electrochemistry*, 1991, pp. 535-579, (H. Lund & M. M. Baizer, eds., Marcel Dekker, 3rd ed., New York, NY).

Streitwieser, Jr., A., et al., Reduction of Imines: Reductive Amination, Introduction to Organic Chemistry, 1981, pp. 748-749, (Macmillan, New York, NY, 2nd Edition).

Van Dam, H.E., et al., Preparation of Platinum of Activated Carbon, *Journal of Catalysis 131*, 1991, pp. 335-349.

Vertes, Cs., et al., Mossbauer Spectroscopy Studies of Sn-Pt/$Al_2O_3$ Catalysts Prepared by Controlled Surface Reactions, *Applied Catalysis*, 1991, pp. 149-159, vol. 68.

Watanabe, M., et al., Electrocatalysis by Ad-Atoms: Part XIII. Preparation of Ad-electrodes with Tin Ad-Atoms for Methanol, Formaldehyde and Formic Acid Fuel Cells, *J. Electroanal. Chem.*, 1985, pp. 367-375, vol. 191.

Database WPI: Section Ch. Week 199918, Derwent Publications Ltd., London, G.B., Class C01, An 1999-215248 XP002900620, and ZA 9 801 219 A (Monsanto Co.), 02/1999 Abstract.

Communication Relating to The Results of the Partial International Search Report for PCT/US99/10242 (mailed Nov. 5, 1999).

Database WPI, Section Ch. Week 199723, Derwent Publications Ltd., London, G.B., Class A41, AN 1997-255484, XP002900970 and JP 09 087215 A(Ube Ind Ltd.), Mar. 31, 1997, abstract, Cycloalkonal and Cycloalkanoe Preparation Useful for High Selectivity by Oxidizing Cycloalkane with Oxygen in the Presence of Ruthenium cpd. and N-Hydroxy Aromatic Acid Imide, for Polyamide gp. High Polymer.

* cited by examiner

PROCESS FOR THE PREPARATION OF N-(PHOSPHONOMETHYL)GLYCINE BY OXIDIZING N-SUBSTITUTED N-(PHOSPHONOMETHYL)GLYCINE

This application is a divisional of U.S. Ser. No. 09/776,801, filed Feb. 5, 2001 now abandoned, which is a divisional of U.S. Ser. No. 09/263,171, filed Mar. 5, 1999, now U.S. Pat. No. 6,232,494, which is a Continuation-in-Part of U.S. Ser. No. 09/023,404, filed Feb. 12, 1998, now U.S. Pat. No. 6,005,140, and which also claims the benefit of U.S. Provisional Ser. No. 60/096,207 filed, Aug. 12, 1998.

BACKGROUND OF THE INVENTION

This invention generally relates to an improved process for reacting N-substituted N-(phosphonomethyl)glycines (sometimes referred to as "N-substituted glyphosates"), salts of N-substituted N-(phosphonomethyl)glycines, and esters of N-substituted N-(phosphonomethyl)glycines to form N-(phosphonomethyl)glycine (sometimes referred to as "glyphosate"), salts of N-(phosphonomethyl)glycine, and esters of N-(phosphonomethyl)glycine via a noble-metal catalyzed oxidation reaction. This invention is particularly directed to such reactions using N-substituted N-(phosphonomethyl)glycines, salts of N-substituted N-(phosphonomethyl)glycines, and esters of N-substituted N-(phosphonomethyl)glycines which have a single N-carboxymethyl functionality.

N-(phosphonomethyl)glycine is described by Franz in U.S. Pat. No. 3,799,758, and has the following formula:

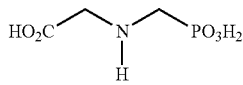

N-(phosphonomethyl)glycine and its salts conveniently are applied as a post-emergent herbicide in an aqueous formulation. It is a highly effective and commercially important broad-spectrum herbicide useful in killing or controlling the growth of a wide variety of plants, including germinating seeds, emerging seedlings, maturing and established woody and herbaceous vegetation, and aquatic plants.

Various methods for the preparation of N-(phosphonomethyl)glycine from N-substituted N-(phosphonomethyl)glycines are known in the art. For example, in U.S. Pat. No. 3,956,370, Parry et al. teach that N-benzylglycine may be phosphonomethylated to N-benzyl N-(phosphonomethyl) glycine, and then reacted with hydrobromic or hydroiodic acid to cleave the benzyl group and thereby produce N-(phosphonomethyl)glycine. In U.S. Pat. No. 3,927,080, Gaertner teaches that N-t-butylglycine may be phosphonomethylated to form N-t-butyl N-(phosphonomethyl)glycine, and then converted into N-(phosphonomethyl)glycine via acid hydrolysis. N-(phosphonomethyl)glycine also may be produced from N-benzyl N-(phosphonomethyl)glycine via hydrogenolysis, as described, for example, in European Patent Application No. 55,695. A separate discussion directed to producing N-(phosphonomethyl)glycine from N-benzyl N-(phosphonomethyl)glycine via hydrogenolysis may be found in Maier, L., *Phosphorus, Sulfur and Silicon*, 61, 65–7 (1991). These processes are problematic in that they produce undesirable byproducts such as isobutylene and toluene which create difficulties due to their potential toxicities. Moreover, acid hydrolysis and hydrogenation of N-substituted N-(phosphonomethyl)glycines have been reported only for hydrocarbyl groups such as tertiary butyl and benzyl groups which are generally known to be susceptible to such reactions; there has not been reported a general method for dealkylation of N-substituted N-(phosphonomethyl)glycines.

Other methods for the preparation of N-(phosphonomethyl)glycine include those directed to oxidatively cleaving N-(phosphonomethyl)iminodiacetic acid (sometimes referred to as "PMIDA"):

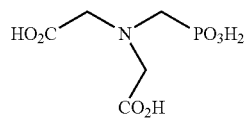

PMIDA may be synthesized, for example, from phosphorus trichloride, formaldehyde, and an aqueous solution of the disodium salt of iminodiacetic acid, as described by Gentilcore in U.S. Pat. No. 4,775,498:

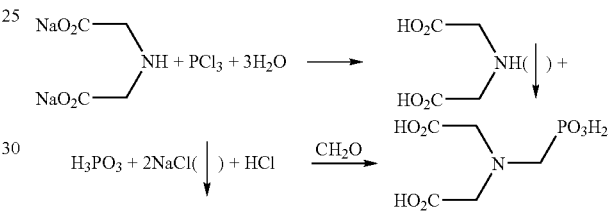

PMIDA

This reaction is complicated by the necessity of removing sodium chloride from the PMIDA product. Sodium chloride has low solubility in the presence of HCl due to the common ion effect, and both iminodiacetic acid and PMIDA are insoluble in HCl and in water under neutral conditions. Thus, salt separation requires that the NaCl be dissolved after the reaction forming PMIDA is complete. This is done by neutralizing the HCl with a base, and then adding water to ensure that all the NaCl dissolves. This large volume of water leads to significant losses of PMIDA during recovery, and increases the volume of waste.

Various methods for converting PMIDA into N-(phosphonomethyl)glycine are well known in the art. These include:
1. Heterogeneous catalytic oxidation. This method is discussed, for example by Franz in U.S. Pat. No. 3,950,402. A separate discussion may be found in Balthazor et al., U.S. Pat. No. 4,654,429.
2. Homogeneous catalytic oxidation. This method is described, for example, in Riley et al., *J. Amer. Chem. Soc.* 113, 3371–78 (1991). A separate discussion may be found in Riley et al., *Inorg. Chem.*, 30, 4191–97 (1991).
3. Electrochemical oxidation using carbon electrodes. This method is described, for example, by Frazier et al. in U.S. Pat. No. 3,835,000.

Such methods oxidatively remove one of the two N-carboxymethyl groups from PMIDA. Generally, such oxidative decarboxylations rely on a one-electron oxidation of PMIDA accompanied by loss of carbon dioxide to form a carbon based radical. The radical is then oxidized to N-(phosphonomethyl)glycine in a subsequent one-electron step. These reactions are summarized as follows:

which forms when $PCl_3$ and $CH_2O$ are used to phosphonomethylate N-substituted glycine salts.

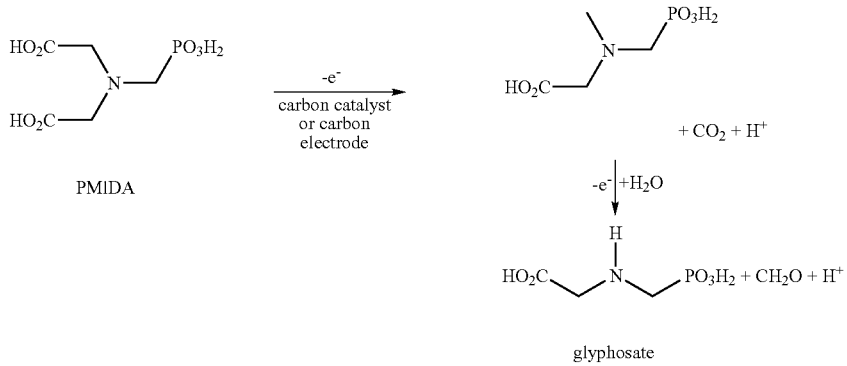

Oxidative decarboxylations, in general, are well known in the art, particularly for electrochemical oxidations (also known as the Kolbe reaction). The Kolbe reaction is particularly facile with carbon electrodes. See, e.g., S. Torii and H. Tanaka, *Organic Electrochemistry*, 535–80 (H. Lund and M. M. Baizer eds., Marcel Dekker, 3rd ed. 1991).

The methods used to oxidize PMIDA to N-(phosphonomethyl)glycine have not been reported to be useful for preparing N-(phosphonomethyl)glycine from N-substituted N-(phosphonomethyl)glycines having only one N-carboxymethyl group, i.e., where R' in the following formula is a functionality other than a carboxymethyl:

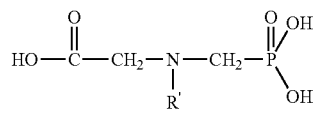

If R' is other than a carboxymethyl, removal of R' typically requires a single, two-electron oxidation of the N-substituted N-(phosphonomethyl)glycine, rather than two successive one-electron oxidations.

SUMMARY OF THE INVENTION

As the foregoing suggests, there is a need for a more general process for oxidizing N-substituted N-(phosphonomethyl)glycines and their salts and esters (sometimes collectively referred to as "N-substituted N-(phosphonomethyl)glycine reactants") to prepare N-(phosphonomethyl)glycine and its salts and esters. Such a process would allow a wider range of N-substituted glycines and salts thereof (sometimes collectively referred to as "N-substituted glycine reactants") to be used as raw materials to make N-(phosphonomethyl)glycine and its salts and esters. Such a process also would allow for N-(phosphonomethyl)glycine to be made from N-methyl N-(phosphonomethyl)glycine (sometimes referred to as "NMG"), an undesirable byproduct from the carbon-catalyzed oxidation of PMIDA. Such a process would further allow for the use of the various N-substituted glycine reactants and N-substituted N-(phosphonomethyl)glycine reactants that—unlike iminodiacetic acid and PMIDA—are soluble in HCl, and therefore more easily separated from the chloride salt byproduct This invention addresses the above-described need. More specifically, this invention provides processes for preparing N-(phosphonomethyl)glycine and its salts and esters by the oxidation of N-substituted N-(phosphonomethyl)glycine reactants having a single N-carboxymethyl functionality. This invention also provides processes for preparing various starting materials used to prepare N-(phosphonomethyl) glycine and its salts and esters. This invention further provides a novel catalyst which may be used to catalyze the oxidation reaction.

Briefly, therefore, in one embodiment directed to a process for preparing N-(phosphonomethyl)glycine, a salt of N-(phosphonomethyl)glycine, or an ester of N-(phosphonomethyl)glycine, the process comprises combining an N-substituted N-(phosphonomethyl)glycine reactant with oxygen in the presence of a catalyst comprising a noble metal on a polymer support. The N-substituted N-(phosphonomethyl)glycine reactant has the formula (V):

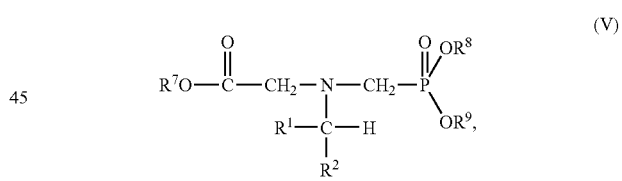

(V)

with $R^1$ and $R^2$ being independently selected from the group consisting of hydrogen, halogen, $-PO_3R^2R^3$, $-SO_3R^{14}$, $-NO_2$, hydrocarbyl, and substituted hydrocarbyl other than $-CO_2R^5$; and $R^7$, $R^8$, $R^9$, $R^{12}$, $R^{13}$, $R^{14}$, and $R^{15}$ being independently selected from the group consisting of hydrogen, hydrocarbyl, substituted hydrocarbyl, and an agronomically acceptable cation.

In another embodiment directed to a process for preparing N-(phosphonomethyl)glycine, a salt of N-(phosphonomethyl)glycine, or an ester of N-(phosphonomethyl)glycine, the process comprises combining an N-substituted N-(phosphonomethyl)glycine reactant with oxygen in the presence of a catalyst comprising a noble metal and a promoter. The N-substituted N-(phosphonomethyl)glycine reactant has the formula (V), as defined in the preceding paragraph. The promoter comprises a metal selected from the group consisting of aluminum, ruthenium, osmium, indium, gallium, tantalum, tin, and antimony. At least about 0.05% by weight of the catalyst consists of the promoter.

In another embodiment directed to a process for preparing N-(phosphonomethyl)glycine, a salt of N-(phosphonomethyl)glycine, or an ester of N-(phosphonomethyl)glycine, the process comprises first contacting a surface of a carbon support with an oxidizing agent, and then depositing a noble metal onto the oxidized surface to form a carbon-supported oxidation catalyst. An N-substituted N-(phosphonomethyl)glycine reactant is then combined with oxygen in the presence of the carbon-supported oxidation catalyst. The N-substituted N-(phosphonomethyl)glycine reactant has the formula (V) (as defined in the preceding paragraphs).

In another embodiment directed to a process for preparing N-(phosphonomethyl)glycine, a salt of N-(phosphonomethyl)glycine, or an ester of N-(phosphonomethyl)glycine, the process comprises combining an N-substituted N-(phosphonomethyl)glycine mixture comprising an N-substituted N-(phosphonomethyl)glycine reactant with oxygen in the presence of a noble metal catalyst in an oxidation reaction zone to form an N-(phosphonomethyl)glycine mixture comprising N-(phosphonomethyl)glycine, the salt of N-(phosphonomethyl)glycine, or the ester of N-(phosphonomethyl)glycine. N-(phosphonomethyl)glycine, the salt of N-(phosphonomethyl)glycine, or the ester of N-(phosphonomethyl)glycine is then separated from the N-(phosphonomethyl)glycine mixture to recover the separated N-(phosphonomethyl)glycine, salt of N-(phosphonomethyl)glycine, or ester of N-(phosphonomethyl)glycine and form a residual mixture. Subsequently, the residual mixture is divided into a recycle mixture and a waste mixture, and the recycle mixture is fed back into the oxidation reaction zone. In this embodiment, the N-substituted N-(phosphonomethyl)glycine reactant has the formula (V) (as defined in the preceding paragraphs).

In another embodiment directed to a process for preparing N-(phosphonomethyl)glycine, a salt of N-(phosphonomethyl)glycine, or an ester of N-(phosphonomethyl)glycine, the process comprises introducing oxygen into a mixture comprising an N-substituted N-(phosphonomethyl)glycine reactant and a noble metal catalyst. Here, the oxygen is introduced into the mixture through a membrane. The N-substituted N-(phosphonomethyl)glycine reactant has the formula (V) (as defined in the preceding paragraphs).

In another embodiment directed to a process for preparing N-(phosphonomethyl)glycine, a salt of N-(phosphonomethyl)glycine, or an ester of N-(phosphonomethyl)glycine, the process comprises forming a reaction mixture by combining an N-substituted N-(phosphonomethyl)glycine reactant with oxygen in the presence of a noble metal catalyst. In this embodiment, no greater than about 10% by volume of the reaction mixture consists of undissolved oxygen. The N-substituted N-(phosphonomethyl)glycine reactant has the formula (V) (as defined in the preceding paragraphs).

In another embodiment directed to a process for preparing N-(phosphonomethyl)glycine, a salt of N-(phosphonomethyl)glycine, or an ester of N-(phosphonomethyl)glycine, the process comprises introducing oxygen into a mixture comprising an N-substituted N-(phosphonomethyl)glycine reactant and a noble metal catalyst in a stirred tank reactor. In this embodiment, the oxygen is introduced into the reactor as gas bubbles in a manner such that essentially no gas bubbles enter a region of the reactor through which an impeller passes. The N-substituted N-(phosphonomethyl)glycine reactant has the formula (V) (as defined in the preceding paragraphs).

In another embodiment directed to a process for preparing N-(phosphonomethyl)glycine, a salt of N-(phosphonomethyl)glycine, or an ester of N-(phosphonomethyl)glycine, the process comprises first combining an N-substituted N-(phosphonomethyl)glycine reactant with oxygen in the presence of a noble metal catalyst in an oxidation reaction zone to form an oxidation product comprising (a) a ketone, and (b) N-(phosphonomethyl)glycine, the salt of N-(phosphonomethyl)glycine, or the ester of N-(phosphonomethyl)glycine. The ketone is then separated from the oxidation product, and used as a starting material to form the N-substituted N-(phosphonomethyl)glycine reactant. This reactant, in turn, is combined with oxygen in the presence of the noble metal catalyst in the oxidation reaction zone. The N-substituted N-(phosphonomethyl)glycine reactant has the formula (V) (as defined in the preceding paragraphs, except that $R^1$ and $R^2$ are independently selected from the group consisting of hydrocarbyl and substituted hydrocarbyl other than —$CO_2R^{15}$).

This invention is also directed to a process for preparing N-(phosphonomethyl)glycine or a salt thereof. In one embodiment, the process comprises first converting an N-substituted glycine salt into an N-substituted glycine free acid. The N-substituted glycine free acid is then phosphonomethylated to form an N-substituted N-(phosphonomethyl)glycine or a salt thereof. Afterwards, the N-substituted N-(phosphonomethyl)glycine or the salt thereof is combined with oxygen in the presence of a noble metal catalyst in an oxidation reaction zone. The N-substituted glycine free acid has the formula (XII):

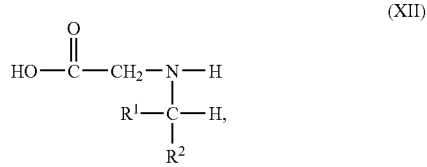

the N-substituted glycine salt has the formula (XIII):

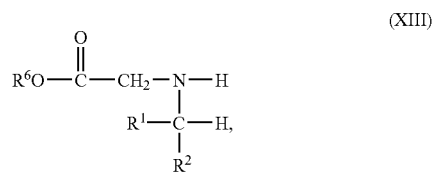

and the N-substituted N-(phosphonomethyl)glycine has the formula (I):

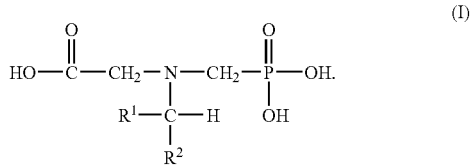

In this embodiment, $R^1$ and $R^2$ are independently selected from the group consisting of hydrogen, halogen, —$PO_3R^{12}R^{13}$, —$SO_3R^{14}$, —$NO_2$, hydrocarbyl, and substituted hydrocarbyl other than —$CO_2R^{15}$; $R^6$ is an agronomically acceptable cation; $R^{12}$, $R^{13}$, and $R^{14}$ are independently selected from the group consisting of hydrogen, hydrocarbyl, and substituted hydrocarbyl; and $R^{15}$ is selected from the group consisting of hydrogen, hydrocarbyl, substituted hydrocarbyl, and an agronomically acceptable cation.

This invention is also directed to a process for preparing an N-substituted N-(phosphonomethyl)glycine or a salt thereof. In one embodiment, the process comprises first combining a source of $H_3PO_3$, a source of $CH_2O$, and an N-substituted glycine salt in a reaction zone to form a first mixture which comprises (a) the N-substituted N-(phosphonomethyl)glycine or the salt thereof, and (b) a salt precipitate. The salt precipitate is separated from the first mixture to form a second mixture which comprises the N-substituted-(phosphonomethyl)glycine or the salt thereof. Base is added to this second mixture to precipitate N-substituted N-(phosphonomethyl)glycine or the salt thereof. The precipitated N-substituted N-(phosphonomethyl)glycine or salt thereof is then separated from the second mixture to recover the precipitated N-substituted N-(phosphonomethyl)glycine or salt thereof and form a residual mixture. Here, the N-substituted N-(phosphonomethyl)glycine has the formula (I) and the N-substituted glycine salt has the formula (XIII) (both formulas being as defined in the preceding paragraph).

In another embodiment directed to process for preparing an N-substituted N-(phosphonomethyl)glycine or a salt thereof, the process comprises first combining a source of $H_3PO_3$ and an N-substituted glycine salt in a reaction zone to form a first mixture which comprises (a) an N-substituted glycine free acid, and (b) a salt precipitate. The salt precipitate is separated from the first mixture to form a second mixture comprising the -substituted glycine free acid. A source of formaldehyde is then added to the second mixture to form a third mixture which comprises the -substituted-(phosphonomethyl)glycine or the salt thereof. A base is added to the third mixture to precipitate N-substituted N-(phosphonomethyl)glycine or the salt thereof. Afterward, the precipitated N-substituted N-(phosphonomethyl)glycine or the salt thereof is separated from the third mixture to recover the precipitated N-substituted N-(phosphonomethyl)glycine or salt thereof and form a residual mixture. The N-substituted N-(phosphonomethyl)glycine has the formula (I), the N-substituted glycine salt has the formula (XIII), and the N-substituted glycine free acid has the formula (XII) (all the formulas being as defined in the preceding two paragraphs).

This invention also is directed to a process for preparing an N-substituted monoethanolamine. In one embodiment, this process comprises combining a ketone, monoethanolamine, and $H_2$ in the presence of a metal-containing catalyst and in a reaction medium consisting essentially of no non-reactive solvent. The N-substituted monoethanolamine has the formula (XI):

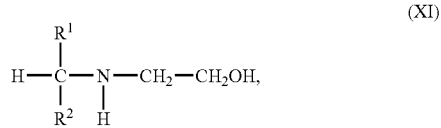

and the ketone has the formula (VIII):

Here, $R^1$ and $R^2$ are independently selected from the group consisting of hydrocarbyl and substituted hydrocarbyl.

This invention is further directed to an oxidation catalyst comprising a noble metal and a hydrophobic electroactive molecular species.

Other features of this invention will be in part apparent and in part pointed out hereinafter.

DETAILED DESCRIPTION OF THE PREFERRED EMBODIMENTS

Figure 1:
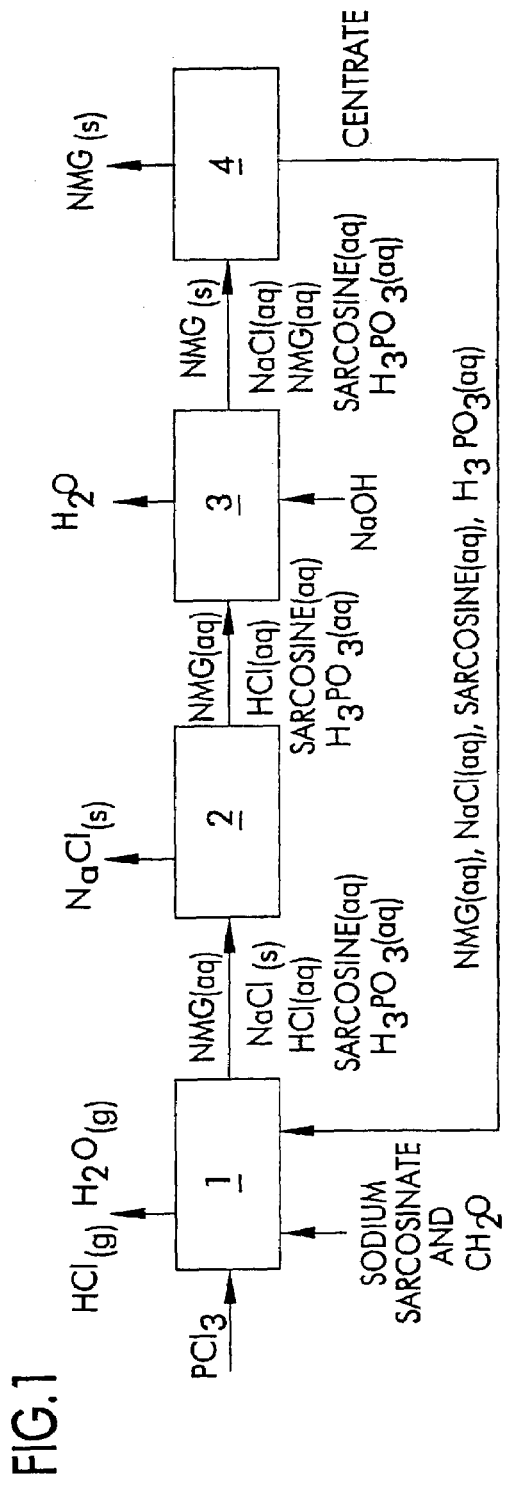
FIG. 1 is a schematic diagram of a preferred embodiment for phosphonomethylating salts of N-substituted glycines.

The present invention provides novel and useful methods for preparing N-(phosphonomethyl)glycine and its salts and esters. These compounds generally have the following formula (IV):

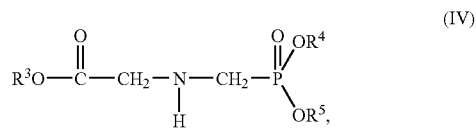

wherein $R^3$, $R^4$, and $R^5$ are independently selected from the group consisting of hydrogen, hydrocarbyl, substituted hydrocarbyl, and an agronomically acceptable cation (more typically, $R^3$, $R^4$, and $R^1$ are independently selected from the group consisting of hydrogen and an agronomically acceptable cation; and even more typically, $R^3$ is selected from the group consisting of hydrogen and an agronomically acceptable cation, and $R^4$ and $R^5$ are hydrogen). The methods of this invention are directed to making these compounds by oxidatively cleaving an N-substituted N-(phosphonomethyl) glycine reactant with oxygen over a noble metal catalyst. Advantages of preparing N-(phosphonomethyl)glycine and its salts and esters from N-substituted N-(phosphonomethyl) glycine reactants using these methods include the simplicity of the procedure, the low cost of the oxidant (e.g., air or molecular oxygen), and the durability of the catalyst (i.e., little or no deactivation of the catalyst over several cycles).

The methods of this invention are not limited to the oxidation of PMIDA (which has two N-carboxymethyl functionalities). Instead, they may be used to make N-(phosphonomethyl)glycine, salts of N-(phosphonomethyl)glycine, or esters of N-(phosphonomethyl)glycine by oxidatively cleaving N-substituted N-(phosphonomethyl) glycine reactants having only one N-carboxymethyl functionality. Thus, a wide range of N-substituted glycine reactants and N-substituted N-(phosphonomethyl)glycine reactants may be used as starting materials in accordance with this invention. This invention also is advantageous because it provides a method to prepare N-(phosphonomethyl)glycine from NMG, an undesirable byproduct from the carbon-catalyzed oxidation of PMIDA. This invention is further advantageous because it may be used with N-substituted glycine reactants and N-substituted N-(phosphonomethyl)glycine reactants that are soluble in HCl, and therefore more easily separated from chloride salts than iminodiacetic acid and PMIDA.

A. Preparation of Various N-Substituted Glycine Reactants

Several methods may be used to prepare N-substituted glycine reactants. The following discussion provides several examples of such methods.

In one embodiment of this invention, the N-substituted glycine reactant is prepared by the condensation of hydrogen cyanide, formaldehyde, and an N-substituted amine, followed by hydrolysis:

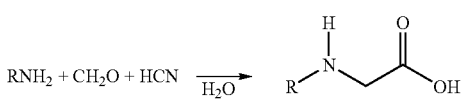

This reaction is known as the Strecker synthesis. The Strecker synthesis is well-known in the art and described in Dyker, G., *Angewandte Chimie Int'l Ed. in English*, Vol. 36, No. 16, 1700–2 (1997) (incorporated herein by reference).

In another embodiment of this invention, an N-substituted glycine is prepared by dehydrogenation of N-substituted ethanolamine in the presence of a base (preferably NaOH):

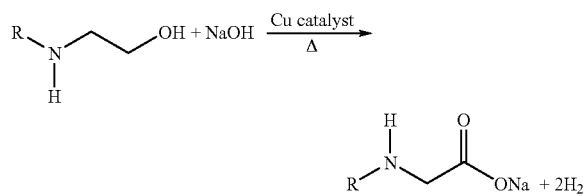

This reaction is described by Franczyk in U.S. Pat. No. 5,292,936 (incorporated herein by reference). An additional separate discussion directed to this reaction may be found in Franczyk, U.S. Pat. No. 5,367,112 (incorporated herein by reference). A further separate discussion may be found in Ebner et al., U.S. Pat. No. 5,627,125 (incorporated herein by reference). The N-substituted ethanolamine precursor may be prepared in at least two ways. First, a ketone may be condensed with monoethanolamine in the presence of hydrogen, a solvent, and a noble metal catalyst. This reaction is described in Cope, A. C. and Hancock, E. M. *J. Am. Chem. Soc.*, 64, 1503–6 (1942) (incorporated herein by reference). N-substituted ethanolamines also may be prepared by combining a mono-substituted amine (such as methylamine) and ethylene oxide to form the mono-substituted ethanolamine. This reaction is described by Y. Yoshida in Japanese Patent Application No. 95-141575 (incorporated herein by reference).

In an alternative embodiment of this invention, an N-substituted amide, formaldehyde, and carbon monoxide are combined in the presence of a catalyst (e.g., a catalyst comprising Co). This amide is then hydrolyzed to form the N-substituted glycine. This reaction is summarized as follows:

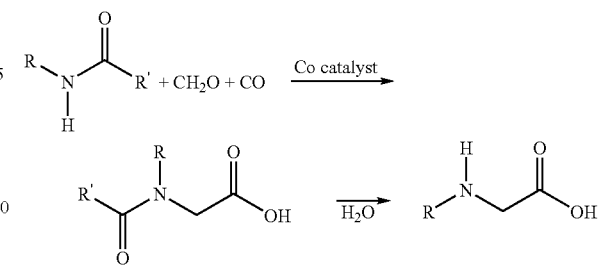

The condensation reaction forming the amide (i.e., "carboxymethylation") is described by Beller et al. in European Patent Application No. 0680948. This reaction also is described in a separate discussion by Knifton, J. F., *Applied Homogeneous Catalysis*, 159–68 (B. Cornils et al. eds., VCH, Weinheim, Germany 1996) (incorporated herein by reference).

In a further embodiment of this invention, the N-substituted glycine reactant is prepared by the reductive alkylation of glycine achieved by combining a carbonyl compound, glycine, and $H_2$ in the presence of a catalyst:

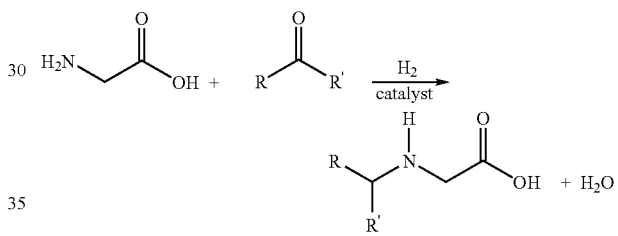

This reaction is described by Sartori et al. in U.S. Pat. No. 4,525,294 (incorporated herein by reference).

B. Preparation of Various N-Substituted N-(phosphonomethyl)glycine Reactants From N-Substituted Glycine Reactants The N-substituted N-(phosphonomethyl)glycine reactants which may be oxidized to form N-(phosphonomethyl)glycine and its salts and esters in accordance with the methods of the present invention generally have the following formula (V):

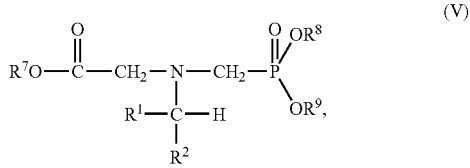

wherein preferably $R^1$ and $R^2$ are independently selected from the group consisting of hydrogen, halogen, $-PO_3R^{12}R^{13}$, $-SO_3R^{14}$, $-NO_2$, hydrocarbyl, and substituted hydrocarbyl other than $-CO_2R^{15}$; and $R^7$, $R^8$, $R^9$, $R^{12}$, $R^{13}$, $R^{14}$, and $R^{15}$ are independently selected from the group consisting of hydrogen, hydrocarbyl, substituted hydrocarbyl, and an agronomically acceptable cation. It should be recognized that $R^1$ and $R^2$ may also together form a ring.

This ring may be either a hydrocarbon ring or a heterocycle, and at least one hydrogen on the ring may be substituted as defined below for substituted hydrocarbyl functionalities.

In a preferred embodiment, $R^1$ is hydrogen; $R^7$, $R^8$, and $R^9$ are hydrogen or an agronomically acceptable cation; and $R^2$ is a linear, branched, or cyclic hydrocarbyl containing up to about 19 carbon atoms. In a more preferred embodiment, $R^7$, $R^8$, and $R^9$ are hydrogen or an agronomically acceptable cation; and —CHR$^1$R$^2$ is selected from the group consisting of methyl (i.e., $R^1$ and $R^2$ are hydrogen), ethyl (i.e., $R^1$ is hydrogen and $R^2$ is —CH$_3$), isopropyl (i.e., $R^1$ and $R^2$ are each —CH$_3$), benzyl (i.e., $R^1$ is hydrogen and $R^2$ is phenyl), and n-pentyl (i.e., $R^1$ is hydrogen and $R^2$ is a 4-carbon, straight-chain hydrocarbyl).

Many N-substituted N-(phosphonomethyl)glycines suitable for use with this invention may be prepared by phosphonomethylating the corresponding N-substituted glycines by, for example, the following reaction:

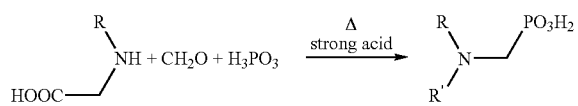

Phosphonomethylation of secondary amines in general is well-known in the art, and discussed at length in Redmore, D., *Topics in Phosphorous Chemistry*, Vol. 8, 515–85 (E. G. Griffith & M. Grayson eds., John Wiley & Sons 1976) (incorporated herein by reference). It is also separately discussed at length in a chapter entitled "α-substituted Phosphonates" in Mastalerz, P., *Handbook of Organophosphorus Chemistry*, 277–375 (Robert Engel ed., Marcel Dekker 1992) (incorporated herein by reference). One example of a secondary amine phosphonomethylation is the phosphonomethylation of iminodiacetic acid to form PMIDA, as taught in Baysdon et al. in U.S. Pat. No. 5,688,994 (incorporated herein by reference).

The phosphonomethylation reaction preferably is conducted at an elevated temperature. The preferred temperature range is from about 100 to about 150° C. The preferred time of reaction is from about 10 to about 120 minutes, with the more preferred reaction time being from about 20 to about 60 minutes. Preferably, the amount of water used for the reaction is minimized to optimize recovery of the N-substituted N-(phosphonomethyl)glycine.

The formaldehyde used in the phosphonomethylation reaction may typically be derived from any source of formaldehyde. Suitable sources of formaldehyde include, for example, formaldehyde itself, formalin, and paraformaldehyde.

The phosphorous acid ($H_3PO_3$) used in the phosphonomethylation reaction also may typically be derived from any source of phosphorous acid. Suitable sources of phosphorous acid include, for example, neat phosphorous acid, phosphorous trichloride, phosphorous tribromide, phosphorous acid esters, chlorophosphonic acid, phosphorous acid esters, chlorophosphonic acid and esters of chlorophosphonic acid. One preferred source is phosphorous trichloride ($PCl_3$), which is particularly preferred where the N-substituted glycine starting material is a salt. When $PCl_3$ is combined with water, the $PCl_3$ is hydrolyzed to form $H_3PO_3$ and 3 equivalents of HCl (the rate of $PCl_3$ addition preferably is determined by the rate at which the HCl gas evolved in the reaction can be safely removed). This hydrolysis reaction is well known in the art and is described in, for example, G. Bettermann, W. Krause, G. Riess, and T. Hofmann, *Ullmann's Encyclopedia of Industrial Chemistry*, vol. A19, p. 527–43 (B. Elvers, S. Hawkins, & G. Schulz, eds., VCH, Weinheim, 5th ed. 1991) (incorporated herein by reference). The following reaction of an N-substituted glycine sodium salt exemplifies the phosphonomethylation of an N-substituted glycine salt reactant using $PCl_3$:

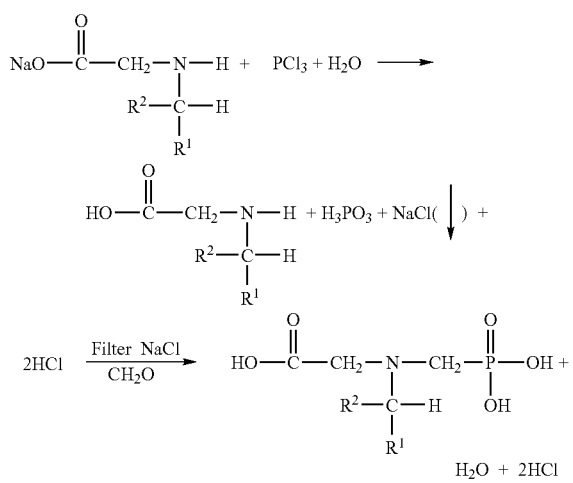

wherein preferably $R^1$ and $R^2$ are independently selected from the group consisting of hydrogen, halogen, —PO$_3$R$^{12}$R$^{13}$, —SO$_3$R$^{14}$, —NO$_2$, hydrocarbyl, and substituted hydrocarbyl other than —CO$_2$R$^{15}$; and $R^{12}$, $R^{13}$, $R^{14}$, and $R^{15}$ are selected from the group consisting of hydrogen, hydrocarbyl, substituted hydrocarbyl, and an agronomically acceptable cation. Other salts besides sodium salts may be used, with salts comprising agronomically acceptable cations being preferred. Alkali metal salts of an N-substituted glycine are especially preferred because of the favorable cost of such salts, and because ammonium salts (a well-known alternative salt) can potentially lead to undesirable side reactions during phosphonomethylation.

The order of adding CH$_2$O and PCl$_3$ to the N-substituted glycine salt solution is not critical (especially where both the N-substituted glycine reactant and N-substituted N-(phosphonomethyl)glycine product are soluble in the presence of HCl), and they may be added in the same or separate reactors (i.e., the "reaction zone" may comprise one or more reactors). In addition, the CH$_2$O may be added to the mixture before or after the chloride salt precipitate is removed (again, especially where both the N-substituted glycine reactant and N-substituted N-(phosphonomethyl) glycine product are soluble in the presence of HCl). It is often most preferred to add the CH$_2$O after the PCl$_3$ has been added and the chloride salt has been removed.

Preferably, approximately equimolar quantities of H$_3$PO$_3$ and the N-substituted glycine reactant are combined with at least an equimolar quantity of CH$_2$O in the presence of a strong acid having a pK$_a$ of no greater than about 1.0. The concentration of the strong acid in the solution preferably is greater than that of the H$_3$PO$_3$, and the number of moles of CH$_2$O added to the reaction mixture preferably is at least 10% greater than the number of moles of either the H$_3$PO$_3$ and the N-substituted glycine reactant, and more preferably is from about 15 to about 25% greater. The CH$_2$O preferably is added to the solution over a period of from about 3 to about 20 minutes as an aqueous solution comprising from about 37% to about 50% CH$_2$O, although both lesser and greater concentrations also may be used.

In one particularly preferred embodiment of this invention, the N-substituted glycine reactant and the resulting N-substituted N-(phosphonomethyl)glycine phosphonomethylation product are soluble in the presence of HCl. Such N-substituted glycines and N-substituted N-(phosphonomethyl)glycines may be easily separated (using, for example, any convenient filtration method) from the NaCl or other chloride salt which precipitates after the PCl$_3$ is added to the solution. This makes phosphonomethylation of such compounds less difficult than phosphonomethylation of iminodiacetic acid to PMIDA using PCl$_3$ (as discussed above in the Background of the Invention section, both iminodiacetic acid and PMIDA are substantially insoluble in the presence of HCl, making salt separation more costly). In an especially preferred embodiment, the N-substituted glycine reactant is selected from the group consisting of sarcosine (i.e., N-methyl glycine) and N-ethyl glycine, with sarcosine being most preferred.

FIG. 1 schematically shows one embodiment that may be used to prepare an N-substituted N-(phosphonomethyl)glycine by combining an N-substituted glycine salt, CH$_2$O, PCl$_3$, and water. For illustration purposes, the N-substituted glycine salt is sodium sarcosinate (i.e., sodium N-methyl glycine). In this embodiment, the PCl$_3$ preferably is introduced into a hydrolyzer reactor 1 comprising a stirred aqueous mixture of CH$_2$O and the sodium N-methyl glycine. The resulting reaction forms HCl and an NaCl precipitate as by-products, in addition to the desired N-methyl N-(phosphonomethyl)glycine ("NMG"). The NaCl precipitate preferably is removed from the mixture using, for example, a filter 2. After the salt precipitate is removed from the solution, the NMG preferably is precipitated by both adding a base (preferably NaOH) to the solution and removing water from the solution (preferably using an evaporator/crystallizer 3). It is preferred not to remove so much water that further salt (e.g., NaCl) produced from the base addition precipitates. The base may be added before, at the same time, or after the water is removed. The amount of base added preferably is the amount required to substantially neutralize the HCl present in the solution. After the NMG precipitates, it preferably is recovered from the solution using, for example, a centrifuge 4. Example 18 further illustrates this phosphonomethylation process.

It should be noted that the process may be varied widely. For example, as noted above, the process may be conducted in a single reaction vessel, or in two or more reaction vessels in series so that, for example, the CH$_2$O and PCl$_3$ are added to the N-substituted glycine salt solution in separate reaction vessels. The N-substituted N-(phosphonomethyl)glycine also may, at least in part, be precipitated by cooling the reaction mixture. Furthermore, the process may be conducted in a batch-wise, semi-batch-wise, or a continuous manner. In a particularly preferred embodiment of this invention, at least a portion of the solution (remaining after removal of the NMG) is recycled back to the hydrolyzer reactor 1 to take advantage of any un-reacted N-methyl glycine reactant which is still present in the solution and to reduce the loss of un-precipitated NMG. The embodiment shown in FIG. 1 includes such a recycle stream.

One particular embodiment of this invention is directed to phosphonomethylating N-substituted glycine salts having the formula (XIII):

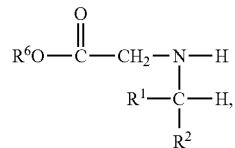

(XIII)

wherein $R^1$ and $R^2$ are independently selected from the group consisting of hydrogen, halogen, $-PO_3R^{12}R^{12}$, $-SO_3R^{14}$, $-NO_2$, hydrocarbyl, and substituted hydrocarbyl other than $-CO_2R^5$; $R^6$ is an agronomically acceptable cation; $R^{12}$, $R^{13}$, and $R^{14}$ are independently selected from the group consisting of hydrogen, hydrocarbyl, and substituted hydrocarbyl; and $R^{15}$ is selected from the group consisting of hydrogen, hydrocarbyl, substituted hydrocarbyl, and an agronomically acceptable cation. In this embodiment, the salt is converted into an N-substituted glycine free acid before being phosphonomethylated. The free acid has the formula (XII):

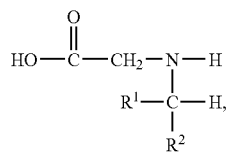

(XII)

wherein $R^1$ and $R^2$ are as previously defined for the N-substituted glycine salt. This embodiment provides a means to avoid the difficulties associated with salts of $R^6$ that form when N-substituted glycine salts are phosphonomethylated directly.

One particularly preferred method for converting an N-substituted glycine salt into the corresponding free acid comprises neutralization of a solution comprising the salt using a cation exchange membrane. More specifically, the solution comprising the N-substituted glycine salt is contacted with one side of a cation exchange membrane while the other side of the membrane is simultaneously contacted with a solution comprising a strong acid which is capable of neutralizing the salt. The two solutions neutralize each other across the membrane, as shown schematically below for a solution comprising an N-substituted glycine sodium salt and a solution comprising an arbitrary acid ("HA"):

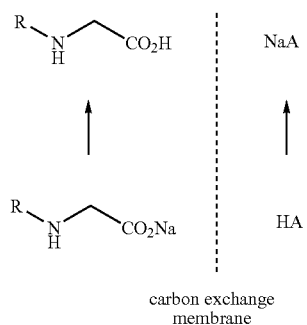

carbon exchange membrane

A stream comprising the N-substituted glycine free acid and a stream comprising a sodium salt of HA are produced. To avoid membrane fouling, the concentration of the N-substituted glycine salt preferably is less than the solubility of the corresponding N-substituted glycine free acid at the neutralization temperature. In addition, the amount of acid used preferably is sufficient to completely neutralize the N-substituted glycine salt, but does not substantially exceed this amount. The strong acid preferably has a pKa of no greater than about 1.0. It is particularly preferred to use non-halogen-containing acids (e.g., methane sulfonic acid, toluene sulfonic acid, nitric acid, sulfuric acid) to avoid contaminating the N-substituted glycine free acid stream with halogens in the event of a torn membrane. Reducing the risk of such contamination is desirable due to the deleterious effect that halogens have on the oxidization catalysts that are used following phosphonomethylation to convert the N-substituted N-(phosphonomethyl)glycine into N-(phosphonomethyl)glycine.

Preferably, the cation exchange membrane is mechanically stable under the reaction conditions (e.g., the membrane preferably does not decompose temperatures of at least about 50° C.), and does not allow the N-substituted glycine salt and free acid to leak across the membrane. Examples of suitable cation exchange membranes are ESC7000 and Sybron MC3470 membranes available from the Electrosynthesis Company of Lancaster, PA; ICE-450 membranes from Gelman Sciences and Neosepta cation exchange membranes from Tokoyama Soda Co. Ltd, Tokyo, Japan; Ionclad and Raipore membranes from Pall Specialty Materials of Port Washington, N.Y.; and Nafion 117, 350, and 450 membranes produced by DuPont Corporation and available from the Electrosynthesis Company and from Aldrich Chemical Co., Milwaukee, Wis. Neutralization via ion exchange (known as "Donnan dialysis") in general is well known in the art, and is described in, for example, K. Scott, *Handbook of Industrial Membranes* at 705 (Elsevier, N.Y., 1995) (incorporated herein by reference).

Electrohydrolysis is an alternative means to convert an N-substituted glycine salt into the corresponding free acid. Conversion of acid salts to the free acid by electrohydrolysis (also known as "electrodialysis") is well known in the art. The general process is described in, for example, H. P. Gregor, *Encyclopedia of Chemical Processing and Design*, 17, 349–63 (J. J. McKetta & W. A. Cunninghams, eds., Marcel Dekker, New York, N.Y. 1983) (incorporated herein by reference). Examples of conversion of amino acid salts to the corresponding free acids by electrohydrolysis may be found in Kuwata et al., U.S. Pat. No. 3,330,749 (incorporated herein by reference). Electrohydrolysis is less preferred than ion-exchange neutralization because electrolysis tends to offer less control over the degree of conversion of the salt to free acid.

Once the N-substituted glycine free acid has been formed by ion exchange neutralization, electrohydrolysis, or another suitable method, it preferably is phosphonomethylated to form an N-substituted N-(phosphonomethyl)glycine having formula (I) or a salt thereof:

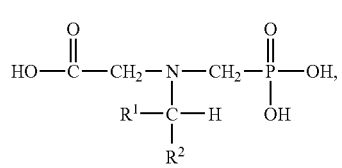

(I)

wherein $R^1$ and $R^2$ are independently selected from the group consisting of hydrogen, halogen, $-PO_3R^{12}R^{13}$, $-SO_3R^{14}$, $-NO_2$, hydrocarbyl, and substituted hydrocarbyl-other than $-CO_2R^{15}$; $R^{12}$, $R^{13}$, and $R^{14}$ are independently selected from the group consisting of hydrogen, hydrocarbyl, and substituted hydrocarbyl; and $R^{15}$ is selected from the group consisting of hydrogen, hydrocarbyl, substituted hydrocarbyl, and an agronomically acceptable cation. The phosphonomethylation preferably is conducted by a process comprising combining the N-substituted glycine free acid, water, a source of $CH_2O$, a strong acid having a $pK_a$ of no greater than about 1.0, and a source of $H_3PO_3$. The source of $H_3PO_3$ may be $PCl_3$, which, for example, may be added directly into a solution comprising the N-substituted glycine free acid. Alternatively, the source of $H_3PO_3$ may be, for example, free of halogens, with neat $H_3PO_3$ or an aqueous solution comprising $H_3PO_3$ being especially preferred. A solution comprising $H_3PO_3$ may be obtained by, for example, hydrolysis of alkyl phosphites, followed by distillation of the alcohols. In a particularly preferred embodiment, the solution is formed by hydrolyzing $PCl_3$ in water in a vessel separate from the solution comprising the N-substituted glycine free acid. Although, about 3 equivalents of HCl are formed when $PCl_3$ hydrolyzes, substantially all the HCl goes into the gas phase and therefore may be readily separated from the hydrolysis reaction mixture. The HCl gas may then be combined with water to form an aqueous HCl solution. Thus, two solutions may be formed with little difficulty: (1) an HCl-containing solution, and (2) an $H_3PO_3$— containing solution having a low halogen (i.e., chloride) concentration. The HCl solution may, in turn, be used as the source of acid for the ion-exchange neutralization of N-substituted glycine salt solutions.

If the source of $H_3PO_3$ is free of halogens, it is particularly preferable for the source of acid for the phosphonomethylation reaction to also be free of halogens. In this instance, $H_2SO_4$ is especially preferred. As noted above, use of such halogen-free acid sources is desirable due to the deleterious effect that halogens have on the oxidization catalysts that are used following phosphonomethylation to convert the N-substituted N-(phosphonomethyl)glycine reactant into N-(phosphonomethyl)glycine.

In general, at the conclusion of a phosphonomethylation reaction, it is preferable to neutralize the strong acid. Neutralization typically aids in the recovery of the N-substituted N-(phosphonomethyl)glycine. Neutralization also tends to reduce the problems associated with the presence of strong acids when the N-substituted N-(phosphonomethyl)glycines are used to synthesize N-(phosphonomethyl)glycine, a salt of N-(phosphonomethyl)glycine, or an ester of N-(phosphonomethyl)glycine; strong acids tend to inhibit the oxidation of N-substituted N-(phosphonomethyl)glycines to N-(phosphonomethyl)glycine.

In a preferred embodiment, the phosphonomethylation reaction mixture is neutralized by using the strong acid present in the mixture as the source of acid to convert (via the cation exchange membrane process discussed above) an N-substituted glycine salt into an N-substituted glycine free acid for subsequent use as a starting material in the phosphonomethylation reaction. In this case, the phosphonomethylation reaction mixture is contacted with one side of the cation exchange membrane while the other side of the membrane is simultaneously contacted with a solution comprising the N-substituted glycine salt:

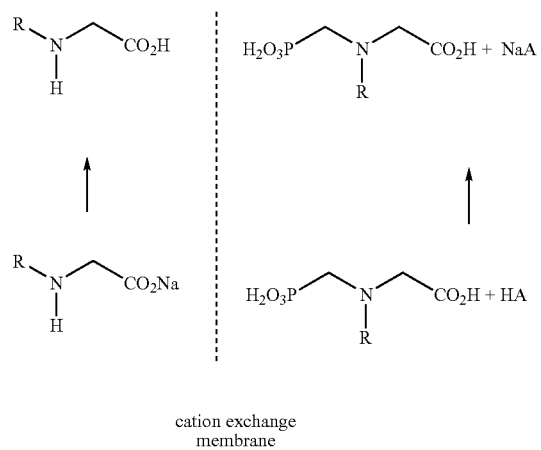

cation exchange membrane

Example 29 further illustrates this embodiment.

Alternatively, the phosphonomethylation reaction mixture may be neutralized by simply adding a base to the reaction mixture after the phosphonomethylation reaction is substantially complete. In this embodiment, if an N-substituted glycine free acid is used as the starting material for the phosphonomethylation, NaOH is typically the preferred base for the neutralization. On the other hand, if an N-substituted glycine salt is used as the staring material, the generally preferred base is the hydroxide of the same cation as in the N-substituted glycine salt. For example, if sodium N-substituted glycinate is used, NaOH would be the preferred base.

The above processes for neutralizing the phosphonomethylation reaction mixture also may be combined. Use of such a combination is preferred when the degree of neutralization achieved by the cation exchange membrane process is less than that required to substantially neutralize all the strong acid in the mixture. In this instance, sufficient base preferably is added to substantially neutralize the strong acid following completion of the cation exchange membrane neutralization process.

Under many circumstances, it is preferred to recover the N-substituted N-(phosphonomethyl)glycine as a solid following the phosphonomethylation. This may be achieved, for example, by forming a reaction mixture containing a supersaturated concentration of the N-substituted N-(phosphonomethyl)glycine (either during phosphonomethylation or after phosphonomethylation) so that the N-substituted N-(phosphonomethyl)glycine will precipitate. Use of such an embodiment is especially preferred when the N-substituted N-(phosphonomethyl)glycine precipitates readily at supersaturated conditions, such as N-methyl N-(phosphonomethyl)glycine. This supersaturation may be achieved by, for example, (1) using a high concentration of the N-substituted glycine reactant (and adding the source of $CH_2O$ after any halogen-containing salt precipitate has been removed); or (2) removing water from the reaction mixture, adding base to the reaction mixture, and/or lowering the temperature of the reaction mixture following the phosphonomethylation and removal of any halogen-containing salt precipitate. Precipitating the N-substituted N-(phosphonomethyl)glycine is often particularly preferable when conducting the phosphonomethylation in a continuous reaction system, which reduces the need for a neutralization step to recover the N-substituted N-(phosphonomethyl)glycine. In this instance, the N-substituted N-(phosphonomethyl)glycine preferably is filtered from the reaction mixture as it precipitates, and the filtrate is returned to the phosphonomethylation reactor. In such a system, preferably a portion of the water in the reaction mixture is removed; this allows a constant volume to be maintained in the phosphonomethylation reaction zone. This removal may be conducted via, for example, evaporation following filtration of the N-substituted N-(phosphonomethyl)glycine. In an especially preferred embodiment, however, at least a portion of the water is removed (e.g., by evaporation) from the reaction mixture before filtration to cause a greater amount of N-substituted N-(phosphonomethyl)glycine to precipitate.

In some circumstances, it is less preferred to recover the N-substituted N-(phosphonomethyl)glycine as a solid following phosphonomethylation. Unlike NMG, some N-substituted N-(phosphonomethyl)glycine reactants (e.g., N-isopropyl N-(phosphonomethyl)glycine) do not precipitate readily, even at supersaturated conditions. In these cases, it is often preferable to neutralize the phosphonomethylation reaction mixture and perform the subsequent catalytic oxidation directly on the neutralized mixture without isolation of the N-substituted N-(phosphonomethyl)glycine reactant as a solid. Under such an approach, it is desirable for the reaction mixture to be free of halogens because, as noted above, halogens tend to have a deleterious effect on the noble metal catalysts used to oxidize the N-substituted N-(phosphonomethyl)glycine reactants. Thus, in such situations, the phosphonomethylation reaction preferably uses a source of $H_3PO_3$ which, in contrast to $PCl_3$, does not contain halogens. Likewise, it is preferred to use an acid during the phosphonomethylation reaction which does not contain halogens ($H_2SO_4$ being especially preferred).

It should be noted that the above phosphonomethylation methods are not the only processes by which N-substituted N-(phosphonomethyl)glycine reactants may be obtained. For example, NMG is produced as an undesirable byproduct from the carbon-catalyzed oxidation of PMIDA.

C. Preparation of N-(phosphonomethyl)glycine and its Salts and Esters by oxidizing N-Substituted N-(phosphonomethyl)glycine Reactants N-(phosphonomethyl)glycine and its salts and esters are prepared in accordance with this invention by oxidizing N-substituted N-(phosphonomethyl)glycine reactants. This oxidation is normally a heterogenous catalysis reaction. Preferably, a solution containing an N-substituted N-(phosphonomethyl)glycine reactant is introduced into a reactor along with an oxygen-containing gas or a liquid comprising dissolved oxygen. In the presence of a noble metal catalyst (i.e., a catalyst comprising a noble metal), the N-substituted N-(phosphonomethyl)glycine reactant is oxidatively converted into N-(phosphonomethyl)glycine and various byproducts:

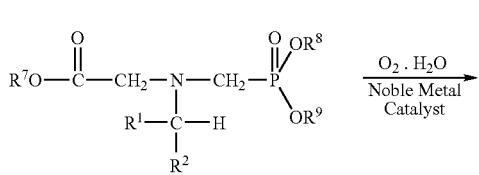

-continued

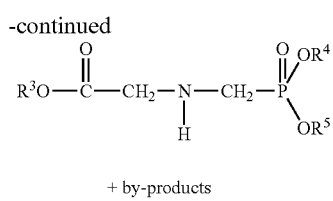

+ by-products wherein preferably $R^1$ and $R^2$ are independently selected from the group consisting of hydrogen, halogen, $-PO_3R^2R^{13}$, $-SO_3R^{14}$, $-NO_2$, hydrocarbyl, and substituted hydrocarbyl other than $-CO_2R^{15}$; and $R^3$, $R^4$, $R^5$, $R^7$, $R^8$, $R^9$, $R^2$, $R^{13}$, $R^{14}$ and $R^{15}$ are independently selected from the group consisting of hydrogen, hydrocarbyl, substituted hydrocarbyl, and an agronomically acceptable cation. Preferably, the catalyst subsequently is separated by filtration and the N-(phosphonomethyl)glycine then is isolated by precipitation, for example, evaporation of a portion of the water and cooling.

The noble metal catalyst preferably comprises a noble metal selected from the group consisting of platinum (Pt), palladium (Pd), rhodium (Rh), iridium (Ir), osmium (Os), and gold (Au). In general, platinum and palladium are more preferred, with platinum being most preferred. Because platinum is most preferred, much of the following discussion will be directed to the use of platinum. It should be understood, however, that the same discussion is generally applicable to the other noble metals and combinations thereof.

The noble metal catalyst may be unsupported, e.g., platinum black, commercially available from various sources such as Aldrich Chemical Co. (Milwaukee, Wis.), Engelhard Corp. (Iselin, N.J.), and Degussa Corp. (Ridgefield Park, N.J.).

Alternatively, the catalyst may comprise a noble metal on the surface of a support, such as carbon, alumina ($Al_2O_3$), silica ($SiO_2$), titania ($TiO_2$), zirconia ($ZrO_2$), siloxane, or barium sulfate ($BaSO_4$). Supported metals are common in the art and may be commercially obtained from various sources, e.g., 5% platinum on activated carbon, Aldrich Catalogue No. 20,593-1; platinum on alumina powder, Aldrich Catalogue No. 31,132-4; palladium on barium sulfate (reduced), Aldrich Catalogue No. 27,799-1; and 5% palladium on activated carbon, Aldrich Catalogue No. 20,568-0. A catalyst comprising a noble metal on a support also may be prepared by depositing the noble metal onto the surface of the support using any of the various methods well-known in the art. Such methods include liquid phase methods such as reaction deposition techniques (e.g., deposition via reduction of noble metal compounds, and deposition via hydrolysis of noble metal compounds), ion exchange techniques, excess solution impregnation, and incipient wetness impregnation; vapor phase methods such as physical deposition and chemical deposition; precipitation; electrochemical deposition; and electroless deposition. Metal deposition methods are described, for example, in Cameron, D. S., Cooper, S. J., Dodgson, I. L., Harrison, B., and Jenkins, J. W. "Carbons as Supports for Precious Metal Catalysts," *Catalyss Today*, 7, 113–137 (1990) (incorporated herein by reference). Metal deposition methods also are described in a separate discussion in Stiles, A. B., *Catalyst Supports and Supported Catalysts, Theoretical and Applied Concepts* (Butterworths, Boston, Mass. 1987) (incorporated herein by reference). A further separate discussion of various methods for depositing metals onto support surfaces may be found in a chapter by R. L. Moss in *Experimental Methods in Catalytic Research*, Vol. 2, Ch. 2, pp. 43–94 (R. B. Anderson & P. T. Dawson, eds., Academic Press, New York, N.Y. 1976) (incorporated herein by reference).

If a carbon support is used, the support preferably is graphitic (such supports tend to have greater N-(phosphonomethyl)glycine selectivity) or has a surface which was oxidized with a strong oxidizing agent before the noble metal was deposited onto the surface. As to the latter type, oxidation of the support may be carried out, for example, by immersing the support in a boiling solution comprising $H_2O_2$. Preferably, at least about 10 wt % (i.e., 10% by weight) of the solution is $H_2O_2$. More preferably, at least about 20 wt % of the solution is $H_2O_2$, and even more preferably, at least about 30 wt % of the solution is $H_2O_2$. The support preferably is immersed in the boiling solution for at least about 15 min., more preferably at least about 30 min., and even more preferably at least about 60 min.

In another particularly preferred embodiment of this invention, the noble metal is supported on a polymeric support (i.e., a support comprising a polymer). The polymeric support preferably is mechanically stable (e.g., the polymer preferably remains hard and is resistant to attrition, thermal degradation, hydrolysis, and acid attack) under the reaction conditions. In addition, the polymer preferably is in the form of cross-linked beads which allow the catalyst to be easily handled, dispersed in the reaction mixture, and filtered following the reaction. Preferably, the beads are porous and have a surface area of at least about 10 $m^2/g$, with the noble metal being well-dispersed on the surface. In one particularly preferred embodiment, the polymer also is basic (i.e., the polymer preferably is capable of being protonated by an acidic noble metal compound), so that it may be readily impregnated with a noble metal (e.g., platinum) using an acidic noble metal compound (e.g., $H_2PtCl_6$). Various polyamides, polyimides, polycarbonates, polyureas, and polyesters may be used as the polymer. Preferably, the polymer is selected from the group consisting of polyethylene imine, salts of polyacrilic acid, polystyrene, polyaminostyrene, polystyrene substituted with dimethylamine groups, sulfonated polystyrene, and polyvinyl pyridine ("PVP"). More preferably, the polymer is selected from the group consisting of PVP and sulfonated polystyrene. In some embodiments, PVP is most preferred.

The noble metal may be deposited onto the polymer support using any of the various well-known methods for depositing a noble metal onto the surface of a support (see above). In a particularly preferred embodiment, the noble metal is platinum and is deposited onto the surface of the support using a solution comprising $H_2PtCl_6$. After the noble metal is deposited onto the support, the support and noble metal preferably are treated with a reducing environment, preferably an aqueous solution comprising sodium borohydride. Examples 20 and 22 further illustrate this method.

The concentration of the noble metal on the surface of a support may vary within wide limits. Preferably it is in the range of from about 0.5 to about 20 wt % ([mass of noble metal÷total mass of catalyst]×100%), more preferably from about 3 to about 15 wt %, and even more preferably from about 5 to about 10 wt %. At concentrations greater than about 20 wt %, layers and clumps of noble metal tend to form. Thus, there are fewer surface noble metal atoms per total amount of noble metal used. This tends to reduce the activity of the catalyst and is an uneconomical use of the costly noble metal.

The weight ratio of the noble metal to the N-substituted N-(phosphonomethyl)glycine reactant in the reaction mixture preferably is from about 1:500 to about 1:5. More preferably, the ratio is from about 1:200 to about 1:10, and even more preferably from about 1:50 to about 1:10.

In a preferred embodiment of this invention, the catalyst may comprise a noble metal and a promoter. The promoter may be on the surface of an unsupported noble metal, or on the surface of the noble metal and/or its support in the case of a supported noble metal catalyst. Noble metal catalysts comprising a promoter often tend to exhibit increased selectivity over noble metal catalysts consisting of a noble metal without a promoter. Preferably, the promoter comprises a metal selected from the group consisting of aluminum (Al), ruthenium (Ru), osmium (Os), indium (In), gallium (Ga), tantalum (Ta), tin (Sn), and antimony (Sb). More preferably, the promoter comprises a metal selected from the group consisting of gallium, indium, ruthenium, and osmium.

Although a promoter may come from various sources (e.g., the catalyst may comprise a support which naturally contains a promoter), it typically is added to the surface of the noble metal (it should be recognized that if the catalyst comprises a support, the promoter typically is added to the surface of the noble metal, the surface of the support, or both). Methods used to deposit the promoter are generally known in the art, and include the same methods which may be used to deposit a noble metal onto a support discussed above. In a particularly preferred embodiment, a solution of a halogen compound of the promoter is used to deposit the promoter by stirring the catalyst in the solution. Examples of suitable halogen compounds that may be used to deposit promoters include: for indium, $InBr_3$; for gallium, $GaBr_3$; for iron, $FeCl_3.6H_2O$; and for tin, $SnCl_2.2H_2O$. Example 25 demonstrates the deposition of a promoter using a solution comprising a halogen compound of the promoter.

The amount of promoter used (whether associated with the noble metal, a support on which the noble metal is deposited, or both) may vary within wide limits, depending in part on the promoter used. Preferably, the weight percentage of the promoter is at least about 0.05% ([mass of promoter÷total mass of the catalyst]×100%).

In one preferred embodiment, the promoter is added to the catalyst by exposing the catalyst precursor to an excess of the promoter so that the maximum amount of promoter is deposited onto the surface of the catalyst.

In another preferred embodiment of this invention, the noble metal catalyst comprises an electroactive molecular species (i.e., a molecular species that may be reversibly oxidized or reduced by electron transfer). Preferably, this electroactive molecular species is on the surface of the noble metal (if the catalyst comprises a support, the electroactive molecular species preferably is on the surface of the noble metal, the surface of the support, or both). It has been discovered in accordance with this invention that selectivity and/or conversion of the noble metal catalyst may be improved by the presence of the electroactive molecular species, particularly where the catalyst is being used to effect the oxidation of NMG to form N-(phosphonomethyl)glycine. In this instance, the electroactive molecular species preferably is hydrophobic and has an oxidation potential ($E_{1/2}$) of at least about 0.3 volts vs. SCE (saturated calomel electrode).

Electroactive molecular species also are useful in the context of the oxidation of N-isopropyl-N-(phosphonomethyl)glycine to form N-(phosphonomethyl)glycine. In that context, it is especially preferable for the catalyst to comprise a noble metal and an electroactive molecular species on a graphitic carbon support. In the presence of the graphitic or oxidized activated carbon support, the electroactive molecular species has been found in accordance with this invention to increase the N-(phosphonomethyl)glycine selectivity of the noble metal catalyst.

Examples of generally suitable electroactive molecular species include triphenylmethane; N-hydroxyphthalimide; 5,10,15,20-tetrakis(pentafluorophenyl)-21H,23H-porphine iron (III) chloride (abbreviated "Fe(III)TPFPP chloride"); 2,4,7-trichlorofluorene; triarylamines, such as N,N'-bis(3-methylphenyl)-N,N'-diphenyl benzidine (sometimes referred to as "TPD") and tris(4-bromophenyl)amine; 2,2,6,6-tetramethyl piperidine N-oxide (sometimes referred to as "TEMPO"); 5,10,15,20-tetraphenyl-21H,23H-porphine iron(III) chloride (sometimes referred to as "Fe(III)TPP chloride"); 4,4'-difluorobenzophenone; 5,10,15,20-tetraphenyl-21H,23H porphine nickel(II) (sometimes referred to as "Ni(II) TPP"); and phenothiazine. When the noble metal catalyst is being used to catalyze the oxidation of NMG to N-(phosphonomethyl)glycine, the particularly preferred electroactive molecular species are triarylamines; N-hydroxyphthalimide; TEMPO; Fe(III)TPP chloride; and Ni(II) TPP. In many embodiments, triarylamines (especially TPD) are the most preferred electroactive molecular species. For example, at reaction temperatures greater than about 130° C., the most preferred electroactive molecular species is TPD.

The oxidation potentials for electroactive molecular species may be found in the literature. A compilation showing the oxidation potential and reversibility for a large number of electroactive molecular species may be found in *Encyclopedia of Electrochemistry of the Elements* (A. Bard and H. Lund eds., Marcel Dekker, New York, publication dates vary between volumes) (incorporated herein by reference). For example, the oxidation potential for triphenylmethane may be found in Perichon, J., Herlem, M., Bobilliart, F., and Thiebault, A., *Encyclopedia of Electrochemistry of the Elements*, vol. 11, p. 163 (A. Bard and H. Lund eds., Marcel Dekker, New York, N.Y. 1978)). Other sources for oxidation potentials include, for example, the following:

1. The oxidation potential for N-hydroxyphthalimide may be found in Masui, M., Ueshima, T. Ozaki, S., *J. Chem. Soc. Chem. Commun.*, 479–80 (1983) (incorporated herein by reference).
2. The oxidation potential for triarylamines may be found in Dapperheld, S., Steckhan, E., Brinkhaus, K., *Chem. Ber.*, 124, 2557–67 (1991) (incorporated herein by reference). A separate source for the oxidation potential for triarylamines is Koene, B. E., Loy, D. E., and Thompson, M. E., *Chem Mater.*, 10, 2235–50 (1998) (incorporated herein by reference).
3. The oxidation potential for 2,2,6,6-tetramethyl piperidine N-oxide may be found in Semmelhack, M., Chou, C., and Cortes, D., *J. Am. Chem. Soc.*, 105, 4492–4 (1983);
4. The oxidation potential for 5,10,15,20-tetrakis(pentafluorophenyl)-21H,23H-porphine iron (III) chloride may be found in Dolphin, D., Traylor, T., and Xie, L., *Acc. Chem. Res.*, 30, 251–9 (1997) (incorporated herein by reference).
5. The oxidation potentials for various porphyrins may be found in Fuhrhop, J. H., *Porphyrins and Metallonorphyrins* 593 (K. Smith, ed., Elsevier, New York, 1975) (incorporated herein by reference).
6. The oxidation potential for phenothiazine may be found in D. Alagli, G. Bazan, M. Wrighton, and R. Schrock, *J. Am. Chem. Soc.*, 114, 4150–58 (1992) (incorporated herein by reference).

An electroactive molecular species may be deposited onto the noble metal catalyst before the catalyst is added to the oxidation reaction mixture. Various methods generally known in the art may be used for this deposition. For example, the electroactive molecular species may be adsorbed onto the catalyst using liquid phase deposition or gas phase deposition. Example 8 illustrates using liquid phase deposition to deposit the electroactive molecular species.

Alternatively, the electroactive molecular species may be added directly to the oxidation reaction mixture separately from the noble metal catalyst. For example, 2,2,6,6-tetramethyl piperidine N-oxide ("TEMPO") may be added to the reaction mixture without first being deposited onto the noble metal catalyst, as illustrated in Example 13. Without being bound by any particular theory, it is believed that in such an embodiment, the electroactive molecular species deposits onto the noble metal catalyst while in the reaction mixture.

The concentration of N-substituted N-(phosphonomethyl) glycine reactant initially in the reaction medium may vary widely. Typically, the concentration is from about 1 to about 80 wt % ([mass of N-substituted N-(phosphonomethyl) glycine reactant÷total reaction mass]×100%). More preferably, the concentration is from about 5 to about 50 wt %, and still more preferably from about 20 to about 40 wt %.

The oxygen source for the oxidation reaction may be, for example, any oxygen-containing gas or a liquid comprising dissolved oxygen. Preferably, the oxygen source is an oxygen-containing gas. As used herein, an "oxygen-containing gas" is any gaseous mixture comprising molecular oxygen which optionally may comprise one or more diluents which are non-reactive with the oxygen, the reactant, and the product under the reaction conditions. Examples of such gases include air, pure molecular oxygen, or molecular oxygen diluted with helium, argon, neon, nitrogen, or other non-molecular oxygen-containing gases. Preferably, at least about 20% by volume of the oxygen-containing gas is molecular oxygen, and more preferably, at least about 50% of the oxygen-containing gas is molecular oxygen.

The oxygen preferably is fed into the reaction mixture at a rate which is sufficient to maintain the dissolved oxygen concentration at a finite level. At reaction temperatures of about 125° C. or below, the oxygen is fed at a rate sufficient to maintain the dissolved oxygen concentration at no greater than about 2.0 ppm, but at a high enough concentration to sustain the desired reaction rate.

The oxygen may be introduced by any convenient means into the reaction medium in a manner which maintains the dissolved oxygen concentration in the reaction mixture at the desired level. If an oxygen-containing gas is used, it preferably is introduced into the reaction medium in a manner which maximizes the contact of the gas with the reaction solution. Such contact may be obtained, for example, by dispersing the gas through a diffuser such as a porous glass or metal frit (preferably having pores which are no greater than about 20 µm in their largest dimension, and more preferably no greater than about 1 µm in their largest dimension), while shaking or stirring the reactor contents to improve liquid-gas contact and dissolution of the oxygen. Less preferred, although suitable, alternative methods for introducing the oxygen include, for example (1) introducing oxygen into the headspace of the reactor and then drawing it into the reaction mixture using a vortex created by an impeller (this method is sometimes described as a back-mixed operation); or (2) passing the oxygen through a tubular reactor packed with catalyst through which the reaction medium also passes.

It has been discovered in accordance with this invention that an excessive amount of oxygen-containing gas bubbles (i.e., undissolved oxygen) can reduce the selectivity of the reaction. Thus, it is preferable to minimize the amount of undissolved oxygen in the solution, and particularly preferable to minimize the amount of undissolved oxygen which comes into contact with the noble metal catalyst. One way to achieve this is to introduced the oxygen through a membrane which is in contact with the solution. The use of membranes for bubble-free gas transfer is discussed generally in, for example, Semmens, M. J. and Gantzer, C. J., in FED Vol. 187, *Aeration Technology*, Book No. G00865, pp. 51–8 (R. E. A. Arndt and A. Prosperetti, eds., 1994) (incorporated herein by reference). The membrane preferably is stable (i.e., does not decompose) under the reaction conditions.

In a particularly preferred embodiment, the reaction is conducted in a stirred-tank reactor employing a rotating impeller and having oxygen-containing gas bubbles introduced into the reaction solution below the upper surface of the solution. To avoid (or at least diminish) the reduction in selectivity due to the oxygen-containing bubbles, the impeller speed preferably is no greater than the speed necessary to prevent the oxygen-containing bubbles from rising directly to the surface of the solution upon their introduction into the solution. Alternatively, oxygen-containing bubbles may be introduced into the solution at a distance from the impeller such that the essentially no bubbles enter the region of the reactor through which the impeller passes, and more preferably such that no bubbles enter the region through which the impeller passes. For example, the oxygen may be introduced just below the upper surface of the liquid and well above the impeller, thereby allowing the bubbles to escape into the headspace rather than forming a gas/liquid turbulent zone around the impeller. Example 27 further illustrates introducing oxygen into a stirred-tank reactor just below the surface of the reaction solution.

The adverse effects of undissolved oxygen also may often be avoided or diminished by introducing oxygen into the reaction mixture in a manner such that no greater than about 10% by volume of the reaction mixture consists of undissolved oxygen. In a more preferred embodiment, no greater than about 4% by volume of the reaction mixture consists of undissolved oxygen, and most preferably, no greater than about 1% by volume of the reaction mixture consists of undissolved oxygen.

The adverse effects of undissolved oxygen in the reaction solution also may often be avoided or diminished by using a noble metal catalyst comprising an electroactive molecular species, as described above. The presence of an electroactive molecular species (particularly N,N'-bis-(3-methylphenyl)-N,N'-diphenyl benzidine) has been found to be especially beneficial for the oxidation of NMG to N-(phosphonomethyl)glycine. Example 27 further illustrates the use of N,N'-bis-(3-methylphenyl)-N,N'-diphenyl benzidine to reduce the adverse effects of undissolved oxygen.

Preferably, the oxidation reaction is conducted at a temperature of from about 50 to about 200° C. More preferably, the reaction is conducted at a temperature of from about 100 to about 190° C., and still more preferably from about 125 to about 160° C.

The pressure in the reactor during the oxidation depends, in part, on the temperature used. Preferably, the pressure is sufficient to prevent the reaction mixture from boiling. If an oxygen-containing gas is used as the oxygen source, the pressure also preferably is adequate to cause the oxygen to dissolve into the reaction mixture at a rate sufficient to sustain the desired rate of reaction. The pressure preferably is at least equal to atmospheric pressure. Preferably, the oxygen partial pressure is from about 5 to about 500 psig.

More preferably, when the temperature is in the range of from about 125 to about 160° C., the oxygen partial pressure is from about 50 to about 200 psig.

The oxidation reaction may be carried out using a wide variety of batch, semi-batch, or continuous reactor systems. Such systems may also include recycling a residual solution remaining after at least a portion of the N-(phosphonomethyl)glycine product has been removed from the reaction product mixture. Recycling the residual solution allows any unreacted N-substituted N-(phosphonomethyl)glycine reactant to be utilized and enhances recovery of any un-precipitated N-(phosphonomethyl)glycine product in the reaction product mixture.

In one embodiment of this invention for continuous systems, only a portion of the residual solution is recycled; the rest is purged. This embodiment is particularly useful for reaction systems in which a contaminant is present in the residual solution. Such a contaminant may, for example, be a salt byproduct which is formed when a strong acid is neutralized following the phosphonomethylation of an N-substituted glycine reactant. If the entire residual solution is recycled back to the oxidation reaction zone, the salt contaminant concentration in the reaction mixture will build up over time. Ultimately, the build up will result in the formation of a salt precipitate which will contaminate the N-(phosphonomethyl)glycine product. To reduce the rate of contaminant build up, a portion of the residual solution may be purged (this purged portion is sometimes referred to as the "waste solution"). The remaining portion (sometimes referred to as the "recycle solution") is recycled back to the oxidation reaction zone. The purging may be achieved by, for example, pressurizing the residual solution and contacting it with a membrane which selectively passes the contaminant to form the waste solution while retaining the N-substituted N-(phosphonomethyl)glycine reactant and the unprecipitated N-(phosphonomethyl)glycine product to form the recycle solution. Because the membrane selectively passes the contaminant and retains the N-substituted N-(phosphonomethyl)glycine reactant and unprecipitated N-(phosphonomethyl)glycine product, the waste solution (also called "the permeate") contains a greater concentration of the contaminant and a lower concentration of the N-substituted N-(phosphonomethyl)glycine reactant and unprecipitated N-(phosphonomethyl)glycine reactant than the recycle solution. Preferably, the membrane has a molecular weight cutoff of less than about 1,000 daltons and is mechanically stable under the reaction conditions. Examples of suitable commercially available membranes include the SelRO membranes, MPF-34 and MPF-36, available from LCI Corporation (Charlotte, N.C.). This embodiment is further described in Example 30.

In another embodiment of this invention, the oxidation reaction is discontinued before complete conversion of the N-substituted N-(phosphonomethyl)glycine reactant is obtained. It has been discovered in accordance with this invention that the activity and selectivity of the catalyst tends to decline as the oxidation reaction nears completion. It has further been discovered, however, that because many N-substituted N-(phosphonomethyl)glycine reactants (including NMG and N-isopropyl N-(phosphonomethyl)glycine) are more soluble than N-(phosphonomethyl)glycine itself (or salts thereof or esters thereof), the decline in activity and selectivity can be overcome by removing the N-(phosphonomethyl)glycine, the salt of N-(phosphonomethyl)glycine, or the ester of N-(phosphonomethyl)glycine before the oxidation is complete. This may be achieved by, for example, removing the catalyst (by, for example, filtration), evaporating a portion of the water in the reaction mixture, and cooling the reaction mixture before there has been less-than-complete conversion. The evaporation and cooling steps precipitate much of the N-(phosphonomethyl)glycine product in the solution, thereby allowing the N-(phosphonomethyl)glycine product to be removed from the reaction solution. The residual solution comprising the un-reacted N-substituted N-(phosphonomethyl)glycine is then recycled back to the oxidation reactor.

Preferably, the N-(phosphonomethyl)glycine is precipitated and removed when from about 20 to about 95% of the N-substituted N-(phosphonomethyl)glycine has been consumed. More preferably, the N-(phosphonomethyl)glycine is precipitated and removed when from about 50 to about 90% of the N-substituted N-(phosphonomethyl)glycine has been consumed, even more preferably when from about 50 to about 80% of the N-substituted N-(phosphonomethyl)glycine has been consumed, and most preferably when from about 50 to about 70% of the N-substituted N-(phosphonomethyl)glycine has been consumed. Lower conversions lead to undesirably high recycle rates, whereas greater conversions (as discussed above) are associated with poor catalyst activity and reduced selectivity.

Figure 2:
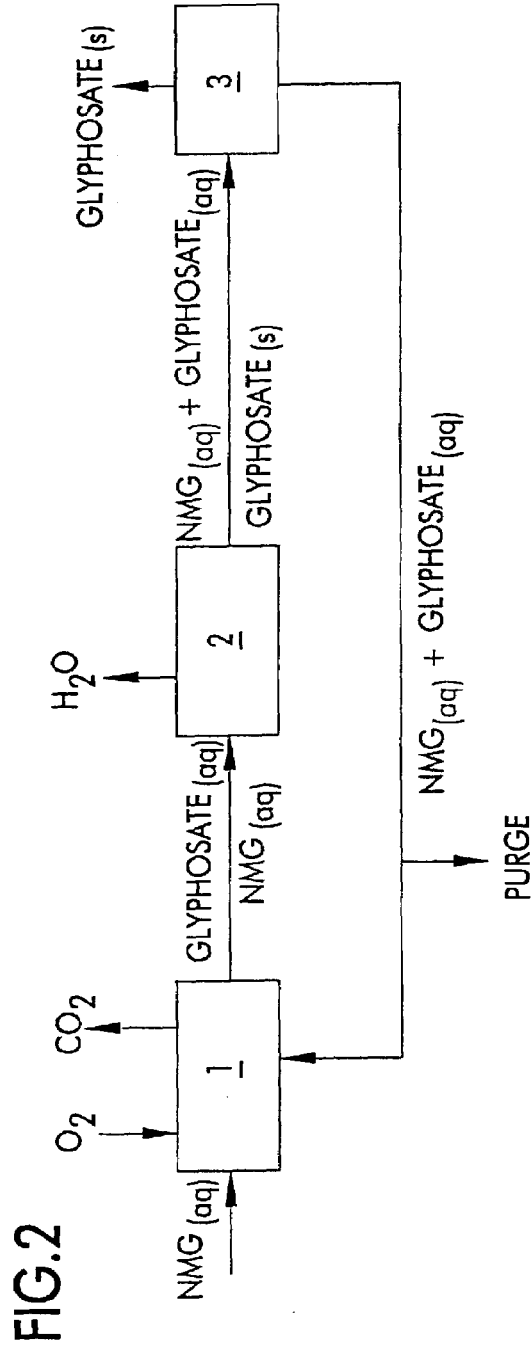
FIG. 2 is a schematic diagram of a preferred embodiment for oxidizing N-substituted N-(phosphonomethyl)glycines wherein (1) the reaction mixture is withdrawn from the oxidation reaction zone before the oxidation is complete, (2) the N-(phosphonomethyl)glycine product in the mixture is precipitated and recovered, and (3) a portion of the mixture is returned to the reaction zone.

A suitable reaction system employing this embodiment is shown schematically in FIG. 2, where, for illustration purposes, the N-substituted N-(phosphonomethyl)glycine reactant is NMG. An aqueous solution of NMG is combined with a heterogeneous noble metal catalyst and heated in the presence of oxygen in an oxidation reactor 1 until the desired conversion (described above) to N-(phosphonomethyl)glycine is achieved. When the desired conversion is achieved, the catalyst is removed by, for example, filtration or centrifugation, and the filtrate is partially evaporated in an evaporator 2 to precipitate at least a portion of the N-(phosphonomethyl)glycine product. The N-(phosphonomethyl)glycine precipitate is then separated from the filtrate by, for example, centrifugation in a centrifuge 3 to recover the N-(phosphonomethyl)glycine and form a second filtrate, which then may be again combined with the noble metal catalyst in the presence of oxygen in the oxidation reactor 1 to continue the oxidation reaction of the NMG still remaining in the second filtrate. In a continuous process, preferably only a portion of the filtrate is fed back into the oxidation reactor; the remaining portion is purged from the system to maintain purity in the reaction system.

A particularly useful method for the production of N-(phosphonomethyl)glycine or a salt thereof involves recycling the ketone which is produced as a by-product when an N-substituted N-(phosphonomethyl)glycine reactant, having a secondary alkyl group as its substituent, is oxidized:

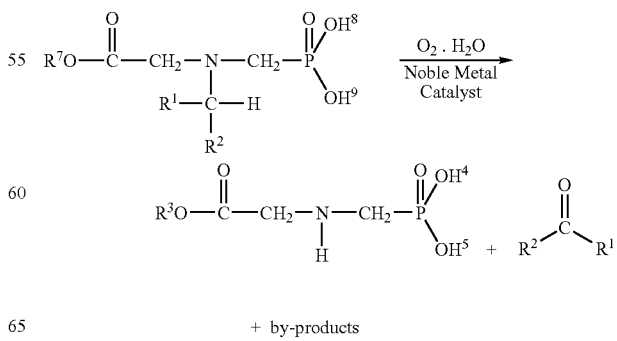

wherein preferably $R^1$ and $R^2$ are independently selected from the group consisting of hydrocarbyl and substituted hydrocarbyl other than —$CO_2R^{15}$; $R^3$, $R^4$, $R^5$, $R^7$, $R^8$, $R^9$ and $R^{15}$ are independently selected from the group consisting of hydrogen, hydrocarbyl, substituted hydrocarbyl, and an agronomically acceptable cation. In this embodiment, the ketone by-product is used as a starting material to further synthesize an N-substituted glycine reactant, which in turn may be phosphonomethylated and then oxidized to form N-(phosphonomethyl)glycine or a salt thereof. Numerous well-known N-substituted glycine synthesis pathways that use ketones as starting materials may be used for this purpose. Typically, the ketone is coupled to an amine by reductive alkylation or reductive amination, a reaction which is well-known in the art. See, generally, A. Streitwieser, Jr. and C. H. Heathcock, *Introduction to Organic Chemistry*, 748 (Macmillan, New York, N.Y., 2nd ed. 1981) (incorporated herein by reference).

In a preferred embodiment of this invention, the ketone is used as a starting material to form the corresponding N-substituted glycine reactant by a reductive alkylation of glycine over a noble metal catalyst, preferably platinum or palladium:

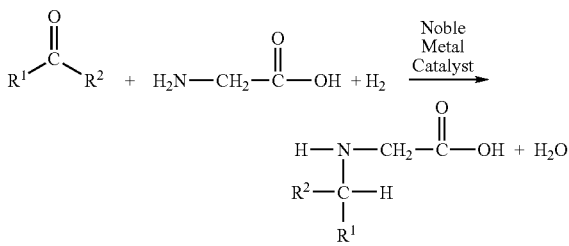

wherein preferably $R^1$ and $R^2$ are independently selected from the group consisting of hydrocarbyl and substituted hydrocarbyl other than —$CO_2R^{15}$; and $R^{15}$ is selected from the group consisting of hydrogen, hydrocarbyl, substituted hydrocarbyl, and an agronomically acceptable cation. This reaction is described, for example, in Sartori et al., U.S. Pat. No. 4,525,294 (incorporated herein by reference).

In a particularly preferred embodiment of this invention, the ketone is reacted with $H_2$ and ammonia in the presence of a metal-containing catalyst to form a primary amine. This primary amine may be converted into an N-substituted glycine by any of the several-methods known in the art. Many of these methods are described in Dyker, G. *Angewandte Chimie Int'l Ed. in English*, Vol. 36, No. 16, 1700–2 (1997) (incorporated herein by reference). Two particularly useful methods are: (1) the Strecker reaction (described above), in which the primary amine is reacted with an aqueous solution of $CH_2O$ and HCN, followed by hydrolysis; and (2) the Wakamatsu reaction, in which the amine is first converted into the corresponding amide, and then reacted with $CH_2O$ and CO over a cobalt or palladium catalyst, followed by hydrolysis.

In a further particularly preferred embodiment of this invention, the ketone is reacted with monoethanolamine and $H_2$ over a solid metal-containing catalyst to form the N-substituted monoethanolamine, which may be converted into a salt of the corresponding N-substituted glycine by combining it with a strong base (preferably NaOH) over a solid copper-containing catalyst:

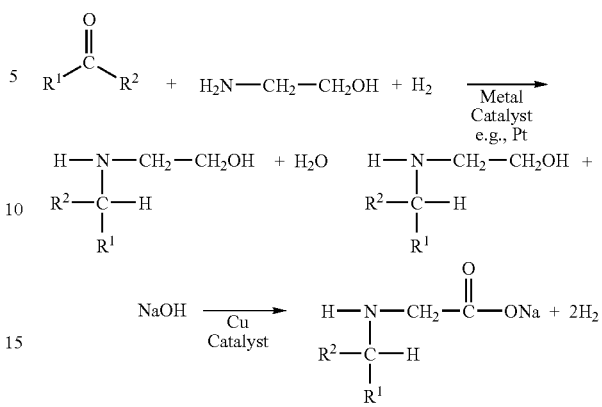

wherein preferably $R^1$ and $R^2$ are independently selected from the group consisting of hydrocarbyl and substituted hydrocarbyl other than —$CO_2R^{15}$; and $R^{15}$ is selected from the group consisting of hydrogen, hydrocarbyl, substituted hydrocarbyl, and an agronomically acceptable cation. As to the first step, Example 28 (below) illustrates such a reductive alkylation of monoethanolamine with ketones and $H_2$ over metal-containing catalysts. This reaction has been shown to be highly selective using ethanol as a solvent. See Cope, A. C. and Hancock, E. M., *J. Am. Chem. Soc.*, 64, 1503–6 (1942) (incorporated herein by reference). Example 28 demonstrates that this reaction also may be conducted over catalysts comprising Pt or Pd essentially in the absence of ethanol or any other non-reactive solvent (i.e., the reaction mixture consists essentially of no non-reactive solvent, and more preferably consists of no non-reactive solvent). As to the second step in the above reaction, the copper-catalyzed dehydrogenation of alcohols to salts of the corresponding carboxylic acids is known in the art and described by Franczyk in U.S. Pat. No. 5,292,936 (incorporated herein by reference). It is separately described in Franczyk, U.S. Pat. No. 5,367,112 (incorporated herein by reference). It is further separately described by Ebner et al. in U.S. Pat. No. 5,627,125 (incorporated herein by reference).

Regardless of the pathway used to synthesize the N-substituted glycine reactant from the ketone by-product, the N-substituted glycine reactant may be phosphonomethylated to form the corresponding N-substituted N-(phosphonomethyl)glycine reactant in accordance with the earlier discussion directed to phosphonomethylating N-substituted glycine reactants.

It should be noted that the methods of this invention have the ability to oxidize N-substituted N-(phosphonomethyl)glycine reactants in the presence of other chemical species which may arise in the course of previously known methods for preparing N-(phosphonomethyl)glycine. For example, these methods have the ability to oxidize NMG in the presence of phosphoric acid and/or phosphonomethylated species that are products of the carbon-catalyzed oxidation of PMIDA, such as aminomethylphosphonic acid ("AMPA"), methyl-aminomethylphosphonic acid ("MAMPA"), and N-(phosphonomethyl)glycine.

Definitions

Unless otherwise stated, the following definitions should be used:

The term "hydrocarbyl" is defined as a radical consisting exclusively of carbon and hydrogen. The hydrocarbyl may be branched or unbranched, may be saturated or unsaturated, and may comprise one or more rings. Suitable hydrocarbyl moieties include alkyl, alkenyl, alkynyl, and aryl moieties. They also include alkyl, alkenyl, alkynyl, and aryl moieties substituted with other aliphatic or cyclic hydrocarbyl groups, such as alkaryl, alkenaryl and alkynaryl.

The term "substituted hydrocarbyl" is defined as a hydrocarbyl wherein at least one hydrogen atom has been substituted with an atom or group of atoms other than hydrogen. For example, the hydrogen atom may be replaced by a halogen atom, such as a chlorine or fluorine atom. The hydrogen atom alternatively may be substituted by an oxygen atom to form, for example, a hydroxy group, an ether, an ester, an anhydride, an aldehyde, a ketone, or a carboxylic acid. The hydrogen atom also may be replaced by a nitrogen atom to form, for example, an amide or a nitro functionality, although substitution by nitrogen to form an amine or a nitrile functionality preferably is avoided. In addition, the hydrogen atom may be replaced with a sulfur atom to form, for example, —$SO_3H$, although substitution by sulfur to form a thiol preferably is avoided.

The term "agronomically acceptable cation" is defined as a cation which allows agriculturally and economically useful herbicidal activity of an N-(phosphonomethyl)glycine anion. An agronomically acceptable cation may be, for example, an alkali metal cations (e.g., a Na ion), an ammonium ion, an isopropyl ammonium ion, a tetra-alkylammonium ion, a trialkyl sulfonium ion, a protonated primary amine, a protonated secondary amine, or a protonated tertiary amine.

EXAMPLES

To further illustrate and explain the invention, several examples are presented below.

General

High pressure liquid chromatography ("HPLC") using an ion exchange separation was used to analyze the products formed during the reactions discussed in the following examples. The analytes were detected using UV/visible detection following post-column reaction to form phosphomolybdate complexes. This method can distinguish between NMG, glyphosate, and phosphoric acid, but cannot distinguish between AMPA and MAMPA because they co-elute. Nevertheless, because AMPA and MAMPA have the same response factor (on a molar basis), the sum of the AMPA and MAMPA concentrations can be reliably determined. This value is reported as (M)AMPA in the examples below.

Example 1

This example illustrates a typical synthesis of NMG.

Approximately 89.09 g of sarcosine (1.00 mole), 82.0 g of phosphorous acid (1.0 mole), and 110 g of concentrated hydrochloric acid were mixed and refluxed in a 130° C. oil bath. Next, 89.3 g of 37% formalin (1.1 mole) was added dropwise over 20 min, and the reaction was continued for an additional 85 min. At this point, NMR revealed the following product distribution (on a molar basis): 89.9% NMG, 2.1% phosphorous acid, 1.9% phosphoric acid, 0.4% hydroxymethyl phosphorous acid, and 5.7% of an unknown product (NMR: triplet, 8.59 ppm). After cooling to room temperature, 40 g of NaOH was added, followed by 250 g of water. This led to the formation of a white precipitate which subsequently was recovered by filtration and assayed by HPLC. The total recovered yield of NMG was 70.5% based on the amount of sarcosine and phosphorous acid used.

Other N-alkyl glyphosates also may be made in a similar manner.

Example 2

This example illustrates the conversion of NMG to glyphosate using a Pt catalyst and oxygen.

Approximately 10.0 g of NMG, 140 g of water, and 1 g of platinum black (Aldrich Chemical Co., Inc., Milwaukee, Wis.) were combined in a round bottom flask equipped with a water-cooled reflux condenser immersed in a 150° C. oil bath. Oxygen was bubbled through for 4 hr as the solution was stirred. At the end of this period, HPLC analysis revealed the following product distributions (on a molar basis): 86.4% glyphosate, 8.7% NMG, 2.2% (M)AMPA, and 2.7% phosphoric acid. Glyphosate precipitated from the solution after cooling to room temperature.

In a second experiment, a mixture of 10.0 g of NMG, 2.0 g of platinum black, and sufficient water to bring the total volume of the mixture to 200 ml, was stirred for 2.7 hr at 80° C. while oxygen was bubbled through the mixture at 1 atm. Analysis of the reaction mixture indicated the following product distribution in molar terms: 85.4% glyphosate, 8.1% phosphoric acid, and 6.5% unknown components. No NMG was detected.

Example 3

This example illustrates the conversion of N-isopropyl glyphosate to glyphosate using a Pt catalyst and oxygen.

Approximately 1.0 g of N-isopropyl glyphosate, 10 g of water, and 0.3 g of platinum black (Aldrich Chemical Co., Inc., Milwaukee, Wis.) were combined in a round bottom flask (equipped with a water-cooled reflux condenser) and immersed in a 80° C. oil bath. A stream of oxygen was introduced at the solution surface for 18 hr as the solution was stirred. At the end of this period, $^{31}P$ NMR revealed the following product distributions (on a molar basis): 91% glyphosate, 1% amino phosphonic acid, 6% phosphoric acid, and 2% unknown product (15.0 ppm). Glyphosate precipitated from solution after cooling to room temperature.

Example 4

Various N-alkyl glyphosates were used under the same conditions as described in Example 3 to produce glyphosate. In other words, the only parameter which was varied was R' in the following formula:

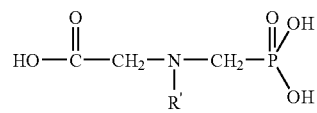

Table 1 shows the alkyl group (i.e., R') used, as well as the conversion and glyphosate selectivity.

TABLE 1

Use of Various N-Alkyl Glyphosates to Prepare Glyphosate

| Alkyl Group | Conversion (%) | Glyphosate Selectivity (%) |
|---|---|---|
| methyl | 91 | 95 |
| isopropyl | 79 | 98 |

TABLE 1-continued

Use of Various N-Alkyl Glyphosates to Prepare Glyphosate

| Alkyl Group | Conversion (%) | Glyphosate Selectivity (%) |
|---|---|---|
| isopropyl | 100 | 91 |
| n-pentyl | 62 | 82 |
| benzyl | 81 | 89 |
| cyclohexyl | 66 | 11 |

Example 5

This example illustrates the conversion of NMG to glyphosate using unsupported platinum and a variety of catalysts in which platinum is dispersed on a non-carbonaceous support.

Approximately 1.0 g of NMG, 10 g of water, and 2.0 g of 5% platinum on barium sulfate were combined in a round bottom flask (equipped with a water-cooled reflux condenser) and immersed in a 95° C. oil bath. Oxygen was bubbled through the reaction for 23 hr as the solution was stirred. At the end of this period, HPLC analysis revealed the following product distributions (on a molar basis): 78.2% glyphosate, 2.4% NMG, 9.4% (M)AMPA, and 10.0% phosphoric acid. Glyphosate precipitated from solution after cooling to room temperature.

In a separate experiment, the data in Table 2 was obtained by heating to reflux a mixture comprising 1 g of NMG, 20 ml of water, and sufficient catalyst to contain 5 mg of platinum metal in a magnetically-stirred, round-bottom flask equipped with a reflux condenser. Oxygen was bubbled through for 5 hr using a needle. The catalyst was then removed by filtration and the filtrate analyzed by HPLC.

As Table 2 indicates, two of the catalysts tested were platinum black catalysts. The Engelhard V2001 (Engelhard Corp., Iselin, N.J.) catalyst has a much smaller surface area than the Aldrich platinum black catalyst (Aldrich Chemical Co., Inc., Milwaukee, Wis.). As the results in Table 2 show, the Engelhard V2001 catalyst had a lower selectivity and conversion, even though 30 times more of the Engelhard catalyst (i.e., 150 mg) was used compared to the Aldrich catalyst (i.e., 5 mg).

TABLE 2

Use of Unsupported and Supported Pt During NMG Oxidation

| Catalyst | Conversion (%) | Glyphosate Select. (%) | (M)AMPA Select. (%) | $H_3PO_4$ Select. (%) |
|---|---|---|---|---|
| Pt black (Aldrich) | 14.7 | 85.3 | 3.0 | 11.7 |
| Pt black (Engelhard V2001) (150 mg) | 2.7 | 70.0 | 17.9 | 12.1 |
| 5% Pt/$SnO_2$ | 18.0 | 88.7 | 2.6 | 8.7 |
| 5% Pt/$ZrO_2$ | 13.9 | 89.5 | 7.3 | 3.2 |
| 5% Pt/$BaSO_4$ | 31.2 | 92.2 | 2.8 | 5.1 |
| 5% Pt/$BaSO_4$ (different catalyst) | 34.0 | 88.6 | 2.8 | 8.7 |
| 5% Pt/$TiO_2$ | 47.4 | 91.9 | 1.7 | 6.4 |
| 5% Pt/$SiO_2$ | 23.7 | 88.9 | 2.3 | 8.8 |

A third experiment was conducted which illustrates that aluminum oxide and siloxanes (Deloxan, Degussa Corp., Ridgefield Park, N.J.) may be used as supports for the metal catalyst. The following experiments were conducted overnight at 95° C. and 1 atm using 1 g of NMG, 10 ml of water, and sufficient catalyst to be equivalent to 0.1 g of platinum metal. Oxygen was introduced through a needle at 50 sccm (i.e., standard $cm^3$ per min.). The resulting solution was filtered and analyzed by HPLC. The dissolved platinum concentration was analyzed by inductively-coupled plasma/mass spectrometry. The results are shown in Table 3.

TABLE 3

Use of Unsupported and Supported Pt During NMG Oxidation

| Catalyst | Conversion (%) | Glyphosate Select. (%) | (M)AMPA Select. (%) | $H_3PO_4$ Select. (%) |
|---|---|---|---|---|
| Pt black (Aldrich) | 98.5 | 85.7 | 6.1 | 8.2 |
| Pt black (Engelhard S3005) | 76 | 82.3 | 11.5 | 6.1 |
| 5% Pt/$SiO_2$ | 82.7 | 79.1 | 11.1 | 9.8 |
| 5% Pt/$SiO_2$ (different catalyst) | 96.7 | 83.6 | 10.6 | 5.9 |
| 5% Pt/$BaSO_4$ | 97.6 | 80.1 | 9.6 | 10.2 |
| 5% Pt/$TiO_2$ | 61.3 | 83.5 | 12.2 | 4.2 |
| 3% Pt/siloxane | 52.4 | 52.8 | 39.2 | 8.0 |
| 5% Pt/siloxane | 57.7 | 70.9 | 26.5 | 2.6 |
| 5% Pt/alumina | 33.8 | 46.7 | 44.4 | 8.9 |
| 5% Pt/alumina (different catalyst) | 48.5 | 37.9 | 50.1 | 5.8 |
| 5% Pt/alumina (different catalyst) | 55.2 | 44.4 | 51.6 | 4.0 |

Example 6

This example illustrates the use of palladium instead of platinum as a catalyst for the oxidation of NMG to glyphosate.

A solution containing of 3.0 g of NMG, 0.3 g of palladium black, and 57 g of water was refluxed in air over a weekend under a water-cooled reflux condenser. NMR analysis indicated the following product distribution (on a molar basis): 97.2% NMG, 2.8% glyphosate, and 0.05% phosphoric acid.

Example 7

This example compares the conversions and selectivities using a catalyst comprising non-graphitic carbon, a catalyst comprising moderately graphitic carbon, and a catalyst comprising graphitic carbon. This example suggests that catalysts comprising graphitic carbon tend to have a better selectivity for glyphosate during the oxidation of NMG.

Three different catalysts comprising platinum dispersed on commercially available carbon supports were used in separate runs to oxidize NMG:
1. 5% Pt/F106 carbon (ethanol washed). F106 carbon and Pt/F106 carbon are available from Degussa Corp. (Ridgefield Park, NJ). F106 carbon is not graphitic.
2. 3% Pt/Sibunit carbon. Sibunit carbon is manufactured as described by Surovikin et al. in U.S. Pat. No. 4,978,649 (incorporated herein by reference), and may be purchased from the Boreskov institute of Catalysis in Novosibirsk, Russia (as can platinum catalysts supported on Sibunit carbon). The carbon is moderately graphitic (i.e., more graphitic than F106 carbon, and less graphitic than Vulcan SC-72R carbon). The particular catalyst used here was prepared by impregnating the carbon with platinum salt, followed by reduction with sodium borohydride. The general preparation of platinum on a carbon support is well-known in the art and is described, for example, in Stiles, A. B., *Catalyst Supports and Supported Catalysts, Theoretical and Applied Concepts* (Butterworths, Boston, Mass. 1987). A separate discussion regarding the general preparation of Pt on a carbon support may be found in a chapter by R. L. Moss in *Experimental Methods in Catalytic Research*, Vol. 2, Ch. 2, pp. 43–94 (R. B. Anderson & P. T. Dawson, eds., Academic Press, New York, N.Y. 1976) (incorporated herein by reference).

3. 20% Pt/Vulcan LX-72R carbon. This catalyst comprises graphitic carbon. It is manufactured by Johnson-Matthey and may be purchased through Alfa/Aesar (Ward Hill, Mass.).

During the NMG oxidations, approximately 100 mg of the catalyst (except as noted), 10 ml of water, and 1 g of NMG were refluxed for 5 hr while oxygen was bubbled through via a needle. The reaction mixture was then filtered and analyzed by HPLC. Table 4 shows the results.

TABLE 4

Use of a Support
Comprising Graphitic Carbon During NMG Oxidation

| Catalyst | Conver. (%) | Glyphosate Select. (%) | (M)AMPA Select. (%) | $H_3PO_4$ Select. (%) |
|---|---|---|---|---|
| 5% Pt/F106 carbon; ethanol-washed (50 mg) | 98.9 | 62.2 | 29.0 | 8.7 |
| 3% Pt/Sibunit carbon | 53.7 | 73.7 | 18.1 | 8.2 |
| 20% Pt/Vulcan XC-72R carbon | 53.6 | 83.5 | 10.4 | 6.1 |

Example 8

This example shows selectivities obtained using a catalyst comprising a noble metal and an electroactive species. All the electroactive molecular species deposited onto platinum black in this example undergo oxidation and reduction by electron transfer. Thus, the treatment of the platinum black by both electroactive molecular species and their oxidative precursors is exemplified herein.

To prepare each organic-treated catalyst (i.e., those containing N-hydroxyphthalimide, tris(4-bromophenyl)amine, TEMPO, triphenylmethane, or 4,4'-difluorobenzophenone), 0.5 g of platinum black (Aldrich Chemical Co., Inc., Milwaukee, Wis.) was added to a solution of 25 mg of the electroactive molecular species in 50 ml of anhydrous acetonitrile. The mixture sat capped in an Erlenmeyer flask for four days (except that the 4,4'-difluorobenzophenone catalyst only was exposed to solution for only one day). The catalyst subsequently was recovered by filtration, rinsed with acetonitrile and diethyl ether, and air-dried overnight.

The 2,4,7-trichlorofluorene catalyst was prepared using 0.3 g of Pt black and 30 ml of a solution containing 834.5 ppm of 2,4,7-trichlorofluorene in acetonitrile/1% $CH_2Cl_2$ solution (used to facilitate dissolution of the electroactive molecular species) which was allowed to evaporate at room temperature. The catalyst subsequently was washed with ethanol and air-dried.

Each inorganic-treated catalyst was prepared by combining 0.50 g of Pt black, 50 ml of tetrahydrofuran, and either 25 or 100 mg of the inorganic electroactive molecular species, and stirring overnight at room temperature in a sealed 125 ml Erlenmeyer flask. The catalyst was recovered by filtration, washed with diethyl ether, and air-dried overnight. The inorganic species used, all of which are available from Aldrich Chemical (Milwaukee, Wis.), were:

1. 5,10,15,20-tetrakis(pentafluorophenyl)-21H,23H-porphine iron (III) chloride (abbreviated "Fe(III)TPFPP chloride" in Table 5). Approximately 25 mg was used to prepare the catalyst.
2. 5,10,15,20-tetraphenyl-21H,23H-porphine iron (III) chloride (abbreviated "Fe(III) TPP chloride" in Table 5). Approximately 25 mg was used to prepare the catalyst.
3. 5,10,15,20-tetraphenyl-21H,23H-porphine nickel (II) (abbreviated as "Ni(II) TPP" in Table 5). Approximately 25 mg was used to prepare the catalyst.
4. Ruthenium-tris(2,2'-bipyridine) dichloride (abbreviated as "[Ru(bpy)$_3$]Cl$_2$" in Table 5). Approximately 100 mg was used to prepare the catalyst.
5. Ferrocene. Approximately 100 mg was used to prepare the catalyst.

Each oxidation was conducted by heating to reflux a mixture containing 1 g of NMG, 20 ml of water, and a catalyst containing 50 mg of platinum metal in a magnetically-stirred, round-bottom flask equipped with a reflux condenser. Oxygen was bubbled through the mixture for 5 hr using a needle. The catalyst was then removed by filtration and the filtrate analyzed by HPLC.

Table 5 shows the results. Where available, literature data on the oxidation potential ($E_{1/2}$) of the electroactive molecular species is reported in Table 5. This example shows that electroactive molecular species which are relatively soluble in water (e.g., ferrocene and Ru(bpy)$_3$]Cl$_2$) tended to be less effective at enhancing glyphosate selectivity. The hydrophobic electroactive molecular species tended to increase the selectivity of the catalyst. Electroactive molecular species having oxidation potentials more negative than about +0.3 V vs SCE tended to decrease conversion. Thus, the preferred electroactive molecular species for enhancing the selectivity and conversion of NMG oxidation may be either organic or inorganic, but preferably are hydrophobic and have oxidation potentials more positive than about 0.3 volts vs. SCE.

TABLE 5

Use of Electroactive Molecular Species on NMG Oxidation

| Poison | $E_{1/2}$ V vs SCE | Conv. (%) | Glyphosate Select (%) | (M)AMPA Select (%) | $H_3PO_4$ Select (%) |
|---|---|---|---|---|---|
| None | — | 45.7 | 83.1 | 9.0 | 7.95 |
| 2,4,7-trichlorofluorene | — | 52.9 | 93.5 | 2.5 | 4.0 |
| N-hydroxyphthalimide | +1.44 | 56.3 | 93.2 | 2.4 | 4.4 |
| tris(4-bromophenyl)amine | +1.05 | 35.3 | 93.5 | 2.5 | 4.0 |

TABLE 5-continued

Use of Electroactive Molecular Species on NMG Oxidation

| Poison | $E_{1/2}$ V vs SCE | Conv. (%) | Glyphosate Select (%) | (M)AMPA Select (%) | $H_3PO_4$ Select (%) |
|---|---|---|---|---|---|
| TEMPO | +0.6 | 71.2 | 92.9 | 2.4 | 4.6 |
| triphenylmethane | +0.27 | 22.1 | 93.4 | ~0 | 6.6 |
| 4,4'-difluorobenzophenone | — | 8.6 | 91.4 | ~0 | 10.9 |
| Fe(III)TPFPP chloride | +0.07 | 22.9 | 89.7 | 4.0 | 6.3 |
| Fe(III)TPP chloride | +1.11 | 69.3 | 91.1 | 2.6 | 6.3 |
| Ni(II)TPP | +1.15 | 53.8 | 90.3 | 2.9 | 6.8 |
| [Ru(bpy)$_3$]Cl$_2$ | +1.32 | 37.9 | 68.9 | 12.1 | 19.1 |
| Ferrocene | +0.307 | 70.8 | 82.6 | 6.0 | 11.4 |

Example 9

This example illustrates the effect of electroactive molecular species on the platinum-catalyzed oxidation of N-isopropyl glyphosate using the commercially available catalyst 20% Pt on Vulcan XC-72R carbon (manufactured by Johnson-Matthey and available from Alfa/Aesar (Ward Hill, Mass.)). The commercial catalyst was compared with a catalyst comprising N-hydroxyphthalimide and a catalyst comprising triphenylmethane.

These catalysts were used to oxidize N-isopropyl glyphosate by the method described in the previous example (approximately 1 g of N-isopropyl glyphosate was substituted for the NMG). The electroactive molecular species improved the selectivity of platinum on carbon catalysts for this reaction. The modifier with less positive oxidation potential (triphenylmethane) was more effective than the modifier with the more positive oxidation potential (N-hydroxyphthalimide). The graphitic support having platinum on its surface was less effective in suppressing undesired side reactions during the oxidation of N-isopropyl glyphosate than it was during the oxidation of NMG (see Example 7).

TABLE 6

Use of Electroactive Molecular Species During Oxidation of N-Isopropyl Glyphosate

| Catalyst | $E_{1/2}$ V vs SCE | Conv. (%) | Glyphosate Select (%) | (M)AMPA Select (%) | $H_3PO_4$ Select (%) |
|---|---|---|---|---|---|
| Platinum black | — | 77.0 | 79.8 | 8.9 | 11.3 |
| 20% Pt/Vulcan XC-72R carbon (25 mg used) | +0.07 | 81.9 | 20.5 | 72.1 | 7.4 |
| 20% Pt/Vulcan treated with N-hydroxyphthalimide loading 35.3 mg/g (26 mg used) | +1.44 | 41.2 | 31.6 | 62.1 | 6.2 |
| 20% Pt/Vulcan treated with triphenylmethane loading 305 mg/g (32.6 mg used) | +0.27 | 60.2 | 50.1 | 25.4 | 24.5 |

Example 10

This example suggests that both selectivity and conversion may be improved by minimizing the dissolved oxygen concentration.

In a 300 mg 316 stainless steel autoclave reactor, 4.4 g of NMG were combined with 1 g of platinum black in 145 g of deionized water. The reaction mixture was heated to 70° C. at 60 psig, and a nitrogen/oxygen mixture was bubbled through the mixture while vigorously mixing the mixture for 4 hr. The dissolved oxygen concentration was measured using an Orbisphere dissolved oxygen probe, calibrated to read 26.4 ppm $O_2$ at 70° C./60 psig air saturation, and controlled by varying the $N_2/O_2$ blend. Two runs were conducted with the dissolved $O_2$ concentration being maintained at 2–3 ppm and 10 ppm. Data from HPLC analysis of the reaction mixture at 2 hrs and 4 hrs is shown in Table 7.

TABLE 7

Minimizing Dissolved Oxygen Concentration During NMG Oxidation

| Dissolved Oxygen Concentration (ppm) | Time (hr) | Conv. (%) | Glyphosate Select (%) | (M)AMPA Select (%) | $H_3PO_4$ Select (%) |
|---|---|---|---|---|---|
| 2.75 | 2 | 66% | 75.96 | 5.48 | 18.56 |
| 2.75 | 4 | 82% | 76.16 | 5.95 | 17.89 |
| 10.4 | 2 | 60% | 70.70 | 14.97 | 14.33 |
| 10.2 | 4 | 76% | 69.83 | 16.21 | 13.97 |

Example 11

This example illustrates the platinum-catalyzed oxidation of N-substituted glyphosates in which the N-substituted group contains atoms other than carbon or hydrogen. In particular, this example describes the oxidation of glyphosine (—HO$_2$CCH$_2$N(CH$_2$PO$_3$H$_2$)$_2$) and N-hydroxyethyl glyphosate, which are prepared by reacting glycine and N-hydroxyethyl glycine, respectively, with CH$_2$O and H$_3$PO$_3$ phosphorous acid in the presence of heat and a strong acid. Phosphonomethylation reactions in general are described in, for example, Redmore, D., *Tonics in Phosphorous Chemistry*, Vol. 8, 515–85 (E. G. Griffith & M. Grayson eds., John Wiley & Sons 1976) (incorporated herein by reference). Phosphonomethylation reactions in general also are described, for example, in a separate discussion in a chapter entitled "α-substituted Phosphonates" in Mastalerz, P., Handbook of Organophosphorus Chemistry, 277–375 (Robert Engel ed., Marcel Dekker 1992) (incorporated herein by reference).

Approximately 1 g of the substrate, 20 ml of water, and 50 mg of platinum black were combined in a round-bottom flask. The oxidation was conducted by the same procedure used for the oxidation of NMG in Example 8. The product distribution was analyzed via $^{31}$P NMR.

Approximately 74.9% of the glyphosine was oxidized with a glyphosate selectivity of 50.2%. The other major product was bis(phosphonomethyl)amine (—HN($CH_2PO_3H_2$)$_2$), which accounted for 39.1% of the oxidized glyphosine. Small quantities of AMPA and of unidentified products also were detected. The use of the platinum black catalyst treated with tris(4-bromophenyl)amine described in Example 8 led to an increase in conversion to 86.8%, but no change in selectivity.

Approximately 46.7% of the N-hydroxyethyl glyphosate was oxidized. The product distribution (on a molar basis) was 61.2% glyphosate, 22.4% N-hydroxyethyl-aminomethylphosphonic acid, and 16.3% phosphoric acid.

Example 12

This example illustrates the rates and selectivities obtained by conducting the oxidation of NMG over platinum black at 125° C. Here, no deactivation of the catalyst was detectable over seven cycles.

A 300 ml glass pressure bottle was equipped with a thermocouple and two fritted filters. One of the filters was located about half an inch above the center of the bottom of the bottle and was used for gas dispersion. The second filter, located about an inch from the bottom and not centered, was used for the withdrawal of liquids. A gas exit line leading to a back pressure regulator set to maintain the pressure at 50 psig also was provided. Approximately 60 g of NMG was loaded into the vessel along with 3 g of platinum black from Aldrich Chemical (Milwaukee, Wis.) and 180 ml of water. The bottle was immersed in an oil bath, magnetically stirred (with a stir bar) and heated under a slow nitrogen flow until the internal temperature reached 125° C., giving a homogeneous solution. Oxygen and nitrogen were then bubbled through the reaction mixture at rates of 1.5 and 0.5 slpm (i.e., standard liters per min.), respectively, for 30 min. The reaction was continued for another 30 min using a flow rate of 1 slpm for both the oxygen and nitrogen. The reaction then was continued for a further 30 min using a nitrogen flow rate of 1.5 slpm and an oxygen flow rate of 0.5 slpm. Stirring was continued and the mixture remained homogeneous throughout the entire 90 min period. A slow nitrogen flow was then established to maintain the pressure. The contents of the bottle were withdrawn through the liquid withdrawal frit, leaving the catalyst in the bottle. About 100 ml of water was injected through the frit and then withdrawn to remove residues from the reaction. The bottle was then allowed to cool. The cycle was repeated 6 more times, each time using 60 g of NMG and 180 ml of water. The results are shown in Table 8.

Platinum concentrations in solution at the end of the runs varied from 0.3 to 1.1 ppm after the first cycle, as determined by inductively-coupled plasma mass spectrometry. Although a greater amount of platinum leached into solution during the first cycle (i.e., the concentration of dissolved platinum was 4.2 ppm), it is believed that most of the lost platinum was primarily unreduced platinum on the surface of the platinum black.

TABLE 8

Repeated Oxidation of NMG over Pt Black at 125° C.

| Run no. | Conversion (%) | Glyphosate Selectivity (%) | (M)AMPA Selectivity (%) | $H_3PO_4$ Selectivity (%) |
|---|---|---|---|---|
| 1 | 89.8 | 82.4 | 5.6 | 12.0 |
| 2 | 80.9 | 87.1 | 3.6 | 9.2 |
| 3 | 84.7 | 79.0 | 8.5 | 12.5 |
| 4 | 66.7 | 83.4 | 5.6 | 11.0 |
| 5 | 79.1 | 81.8 | 7.6 | 10.6 |
| 6 | 75.6 | 79.5 | 7.3 | 13.2 |
| 7 | 78.1 | 79.4 | 9.0 | 11.6 |

Example 13

This example shows the selectivities, conversions, and noble metal loss obtained for the oxidation of N-substituted glyphosates using low rates of oxygen delivery, moderate conversion, and an electroactive molecular species (i.e., 2,2,6,6-tetramethyl piperidine N-oxide). The electroactive species was added directly to the reaction mixture; thus, there was no pretreatment of the catalyst with an electroactive molecular species.

Approximately 60 g of NMG, 180 ml of water, 3 g of platinum black (Aldrich Chemical, Milwaukee, Wis.), and 40 mg of TEMPO (dissolved in 1 ml of acetonitrile) were combined in the pressure reactor described in Example 12. The mixture was heated to 125° C. while stirring under a 50 psig nitrogen atmosphere, forming a homogeneous mixture. A nitrogen/oxygen mixture (75% nitrogen, 25% oxygen by volume) was bubbled through the mixture for 90 min at a flow rate of 1 slpm while the pressure was maintained at 50 psig. The reaction mixture then was withdrawn through a fritted filter, leaving the catalyst behind. Another 60 g of NMG, 180 ml of water, and 40 mg of TEMPO (in 1 ml of acetonitrile) subsequently was added to the flask and the cycle was repeated. Four cycles in all were performed. In all cases, (M)AMPA concentrations were below quantifiable limits, although traces were detected. The only quantifiable byproduct detected was phosphoric acid. The conversions and selectivities at the end of each of the four cycles are shown in Table 9.

As in Example 12, the concentration of dissolved platinum was determined at the end of each run by inductively-coupled plasma mass spectrometry. This dissolved platinum concentration was less than 0.1 ppm in cycles 2, 3, and 4. This is less than the leaching observed in Example 12. As with Example 12, a greater amount of platinum leached into solution during the first cycle (i.e., the concentration of dissolved platinum was 8.3 ppm), although it is again believed that most of the lost platinum was primarily unreduced platinum on the surface of the platinum black.

TABLE 9

Oxidation of NMG in the Presence of TEMPO at 125° C. for 90 Min.

| Cycle Number | Conversion (%) | Glyphosate Selectivity (%) | $H_3PO_4$ Selectivity (%) |
|---|---|---|---|
| 1 | 32.6 | 98.3 | 1.7 |
| 2 | 38.0 | 98.1 | 1.9 |
| 3 | 43.3 | 98.1 | 1.9 |
| 4 | 46.2 | 97.3 | 2.7 |

Example 14

This example shows the selectivities obtained when NMG was prepared via the direct phosphonomethylation of sarcosine amides (e.g., N-acetyl and N-propionyl sarcosine or sarcosine anhydride), rather than sarcosine itself.

Approximately 20.0 g of N-acetyl sarcosine (152.5 mmole), 12.5 g of phosphorous acid (152.4 mmole), and 37.6 g of concentrated hydrochloric acid were mixed and refluxed in a 120° C. oil bath. Approximately 13.6 g of 37% formalin (167.6 mmol) was added dropwise over 20 min. The reaction was continued for an additional 19 hr. HPLC analysis revealed a 99% yield of NMG based on moles charged.

Under the same conditions, 20.0 g N-propionylsarcosine (137.8 mmole) was converted into NMG using 11.3 g of phosphorous acid (137.8 mmole), 10.0 g of concentrated hydrochloric acid, and 12.3 g of 37% formalin (152.1 mmole). HPLC analysis revealed a 96.6% yield of NMG based on moles of N-propionylsarcosine charged.

Also under the same conditions, 2.06 g of sarcosine anhydride (14.50 mmole) was converted into NMG using 2.38 g of phosphorous acid (29.02 mmole), 5.7 g of concentrated hydrochloric acid, and 2.6 g of 37% formalin (32.02 mmole). HPLC analysis revealed a 97.2% yield of NMG based on moles of sarcosine anhydride charged.

In an additional experiment, 2.0 g of N-acetyl sarcosine (15.3 mmole) and 1.25 g of phosphorous acid (15.3 mmole) were mixed with 3.1 g of concentrated sulfuric acid and 1.7 g of water, and then refluxed in a 120° C. oil bath. Approximately 1.4 g of 37% formalin (16.7 mmol) was added dropwise over 20 min. The reaction was continued for an additional 18 hr. $^{31}$P NMR analysis revealed a 98% yield of NMG based on moles of N-acetyl sarcosine charged.

Example 15

This example demonstrates the oxidization of NMG under conditions very similar to those of Example 12, except that a sub-stoichiometric amount of base is present in the reaction mixture.

Approximately 60 g of NMG, 9.6 g of 28–30% ammonium hydroxide (0.25 equivalents), and 170 ml of water were combined in the apparatus described in Example 12 and stirred for 1 hr at an internal temperature of 125° C. while 0.75 slpm of pure oxygen was bubbled through the mixture at a pressure of 50 psig. HPLC analysis of the reaction mixture indicated that 23.5% of the NMG had been oxidized with a selectivity to glyphosate of 65.7%. The selectivities of (M)AMPA and $H_3PO_4$ were 21.1% and 13.2%, respectively.

As the results indicate, the NMG oxidation proceeds, although conversion and selectivity were less than those that may be obtained in the absence of base.

Example 16

This example demonstrates that NMG may be oxidized selectively to glyphosate in the presence of glyphosate and similar compounds. One gram of platinum black was combined with 300 g of a solution containing about 6% NMG and lower quantities of glyphosate, AMPA, MAMPA, formaldehyde, formic acid, and sodium chloride. The mixture was heated to 150° C. for 4 hr while oxygen was passed through the reactor at a pressure of 70 psig. At the conclusion of the reaction, NMR and HPLC analysis indicated that most the NMG had been converted into glyphosate.

Example 17

This example shows the effect of Pt loading on the oxidation of NMG in a 300 ml stirred autoclave reactor equipped with fritted tubes for gas introduction and liquid withdrawal. The liquid withdrawal frit was located below the stirrer and the gas introduction frit was located above and to the side of the stirrer.

Approximately 160 g of an aqueous NMG suspension (25 wt % NMG) was combined with a variable amount of platinum black (Aldrich Chemical, Milwaukee, Wis.). The reactor was closed and pressurized to 85 psig with $N_2$, and heated to 150° C. while stirring at 1000 rpm. When the temperature had stabilized, the gas was switched to 400 sccm of a 25/75 mixture of oxygen and nitrogen (on a molar basis). The reaction was continued for about 80 min.

Table 10 shows the results. The selectivity was only weakly dependent on catalyst loading except at the very lowest loadings, where selectivity deteriorated. Conversion increased with increasing catalyst loading, but less steeply.

TABLE 10

Effect of loading on the oxidation of 25% NMG over platinum black at 150° C.

| Pt loading (g) | Rxn time (min.) | Conv. (%) | Selectivity (%) | | |
|---|---|---|---|---|---|
| | | | Glyphosate | (M)AMPA | $H_3PO_4$ |
| 1.875 | 81 | 61.9 | 88.3 | 3.6 | 8.1 |
| 0.939 | 80 | 50.4 | 91.8 | 1.8 | 6.4 |
| 0.703 | 80 | 47.9 | 91.1 | 2.4 | 6.4 |
| 0.469 | 80 | 36.7 | 90.7 | 2.0 | 7.2 |
| 0.236 | 80 | 24.8 | 83.8 | 2.7 | 13.5 |
| 0.117 | 160 | 28.8 | 79.9 | 5.0 | 15.1 |

Example 18

This example describes the reaction between $PCl_3$ and aqueous sodium sarcosinate to form $H_3PO_3$, HCl, sarcosine, and precipitated NaCl. It also demonstrates the near-quantitative removal of NaCl by filtration.

Approximately 200.5 g of sarcosine and 90.03 g of NaOH (i.e., 2.25 moles each) were combined with 209.4 g of water to make 500 ml of a 50 wt % solution of sodium sarcosinate. The solution was mechanically stirred in a glass vessel while 324.7 g of $PCl_3$ was pumped continuously into the solution below the surface of the solution over 61 min. Upon completion of the $PCl_3$ addition, the temperature of the mixture was 109° C. Sodium chloride crystallized during the addition. The mixture was filtered immediately after the conclusion of the $PCl_3$ addition using two glass fritted Buchner funnels, and the salt cake was sucked dry on the filters without rinsing.

The cake contained 6.8 wt % $H_3PO_3$, and an equal number of moles of sarcosine. The chloride content of the filter cake was determined by dissolving a sample in water and titrating with silver nitrate. This analysis indicated that the cake was 85 wt % NaCl, corresponding to a dry weight of NaCl of 133.2 g (2.28 moles). Thus, approximately all the NaCl formed in the reaction was removed by filtration.

Example 19

This example shows the use of a Pt on carbon catalyst prepared by depositing Pt on activated carbon which has been subjected to a vigorous oxidation. This example also shows the results obtained by treating this catalyst with various metal halides.

Approximately 15–20 g of KB-FF carbon (Norit Americas Inc., Atlanta, Ga.) was placed into a 500 ml Erlenmeyer flask. The carbon was slowly wetted with 30% $H_2O_2$. A minimal amount heat was generated. More 30% $H_2O_2$ was added until the volume of the suspension was approximately 150 ml. The $H_2O_2$ solution then was brought to a boil on a hot plate for approximately 2 hr. Afterward, the hot plate was turned off, and the carbon was allowed to stand overnight in the $H_2O_2$ solution. The following day the carbon was filtered on a glass frit, rinsed with deionized water, and dried in a vacuum oven at 100° C.

Approximately 4.6 g of the carbon was placed into an Erlenmeyer flask. Deionized water was added to produce a dilution of the carbon of at least 30:1 (water to carbon). The pH was adjusted to 6.5 with aqueous KOH. Approximately 2.335 g of $H_2PtCl_6$ was dissolved in 160 ml of water in a separate beaker, and the pH adjusted to 11 with 45% aqueous KOH. The Pt solution was slowly added to the stirring carbon in 10–20 ml aliquots over a 5 hr period. The pH was periodically adjusted to 8–8.5 with 45 wt % KOH. The mixture was stirred overnight. The pH was adjusted to 10.3 in the morning, and stirring was continued for 2 more hours while the pH was maintained at 10.2 using 45% KOH. The mixture was then heated rapidly to 85° C., and a 5 ml aliquot of 37% $CH_2O$ solution was added. The solution was brought to a boil as rapidly as possible. After 10 min. of boiling, another 5 ml of 37% $CH_2O$ was added. The pH was checked several times and adjusted to between 8.5 and 10 while boiling. After boiling for 1 hr, the mixture was cooled and filtered on a glass frit. The catalyst was washed with deionized water and dried in a vacuum oven. This process yielded an 18.9% Pt/C catalyst.

A sample of the catalyst was further modified with metal halides by the procedure in Example 25, except that 0.3–0.5 g of catalyst was used. Approximately 100 mg of each of these catalysts was used to oxidize 1.0 g of NMG in 20 ml of water to form glyphosate. Each run was conducted for 5 hr in a 50 ml round-bottom flask equipped a water-cooled reflux condenser. Oxygen was bubbled through the reaction mixture for the entire 5 hr at reflux. At the completion of each run, the reaction mixture was filtered to remove the catalyst.

Table 11 shows the results. The $GaBr_3$ enhanced both selectivity and conversion. The $AlBr_3$ decreased conversion and had no significant effect on selectivity. The $NbCl_5$ was detrimental to selectivity.

TABLE 11

Screening of NMG Oxidation Activity of Pt Catalysts on Norit KB-FF Carbon Oxidized with 30% $H_2O_2$

| Treatment | Conv. (%) | Glyphosate Selectivity (%) | (M)AMPA Selectivity (%) | $H_3PO_4$ Selectivity (%) |
|---|---|---|---|---|
| None | 41.6 | 90.2 | 3.4 | 6.4 |
| $AlBr_3$ | 28.9 | 88.9 | 4.0 | 7.1 |
| $GaBr_3$ | 57.0 | 93.6 | 2.9 | 3.5 |
| $NbCl_5$ | 49.7 | 70.0 | 23.9 | 6.1 |

Example 20

This example describes the preparation and use of Pt on PVP catalysts. In this example, the PVP support was ground in a blender to increase its surface area, and the Pt was deposited primarily onto the surface of the PVP.

Twenty-five grams of wet Reillex HP polymer (as received from Reilly Industries, Indianapolis, Ind.) was suspended in 100 ml of water and ground in a blender for 20 min. Approximately 1.56 g of $H_2PtCl_6$ (Aldrich Chemical, Milwaukee, Wis.), with a nominal platinum metal content of a least 37.5 wt %, was added to the polymer suspension in a 250 ml round-bottom flask. The light yellow color of $H_2PtCl_6$ transferred entirely to the resin within 1 min, indicating complete take-up of $H_2PtCl_6$ by the PVP resin. Three crams of 12 wt % $NaBH_4$ in 14 molar NaOH (Aldrich Chemical) was then added. The resin turned black instantly as the $NaBH_4$ reduced the Pt. After stirring for 1 hr, the mixture was filtered, and the solid was washed with water. The catalyst then was dried under vacuum at 105° C. Approximately 7.25 g of catalyst was recovered. Analysis by ICP-MS indicated that the catalyst was 3.5 wt % Pt.

Various loadings of the catalyst were used to oxidize 1.0 g of NMG in 20 ml of water to form glyphosate. Each run was conducted for 5 hr in a 50 ml round-bottom flask equipped a water-cooled reflux condenser. Oxygen was bubbled through the reaction mixture for the entire 5 hr at reflux. At the completion of each run, the reaction mixture was filtered to remove the catalyst. For comparison purposes, separate runs using platinum black (Aldrich Chemical) as a catalyst also were conducted under the same reaction conditions.

The results are shown in Table 12. The PVP-supported catalyst was more active per gram Pt than the platinum black, while exhibiting selectivity very close to that of platinum black.

TABLE 12

PVP Supported Platinum Catalyst vs. Platinum Black Catalyst

| Catalyst | Catalyst Loading (mg) | Pt loading (mg) | Conv. (%) | Glyphosate Selectivity (%) | (M)AMPA Selectivity (%) | $H_3PO_4$ Select (%) |
|---|---|---|---|---|---|---|
| 3.5% Pt/Reillex HP | 100 | 3.5 | 19.9 | 70.9 | 12.0 | 17.1 |
| same | 200 | 7.0 | 43.7 | 79.3 | 7.3 | 13.4 |
| same | 300 | 10.5 | 70.8 | 82.1 | 6.3 | 11.6 |
| same | 400 | 14.0 | 71.1 | 79.9 | 6.9 | 13.2 |
| same | 500 | 17.5 | 85.5 | 83.2 | 5.7 | 11.2 |
| Platinum black | 5 | 5 | <1 | — | — | — |
| same | 10 | 10 | <1 | — | — | — |

TABLE 12-continued

PVP Supported Platinum Catalyst vs. Platinum Black Catalyst

| Catalyst | Catalyst Loading (mg) | Pt loading (mg) | Conv. (%) | Glyphosate Selectivity (%) | (M)AMPA Selectivity (%) | $H_3PO_4$ Select (%) |
|---|---|---|---|---|---|---|
| same | 20 | 20 | 57.5 | 86.1 | 3.7 | 10.1 |
| same | 30 | 30 | 74.8 | 95.2 | 3.6 | 1.2 |
| same | 50 | 50 | 80.6 | 84.2 | 4.0 | 11.8 |
| same | 100 | 100 | 84.0 | 90.7 | 2.3 | 7.0 |

Note:
The selectivity of NMG could not be reliably determined for conversions less than 1%.

Example 21

This example demonstrates that the catalyst of Example 20 is an active and selective catalyst for the oxidation of NMG to glyphosate at 125 and 150° C. This example also compares conversions and selectivities for different oxygen concentrations.

Approximately 4.501 g of the catalyst from Example 20 was combined with 116.6 g of water, 40.06 g of NMG, and 0.65 ml of a 0.041 g/ml solution of TEMPO in acetonitrile in a 300 ml stirred autoclave equipped with fritted tubes for gas introduction and liquid withdrawal. The liquid withdrawal frit was located below the stirrer, and the gas introduction frit was above and to the side of the stirrer. The reactor was closed and pressurized to 85 psig with nitrogen and heated to 125° C. while stirring at 1000 rpm. When the temperature had stabilized, the gas was switched to 400 sccm of a 25/75 mixture of oxygen and nitrogen (on a molar basis). After 37 min, the temperature set point was raised to 150° C. The reactor reached 150° C. 8 min later. One hour into the run, the composition of the gas mixture was changed to 37.5% oxygen in nitrogen at the same total flow rate.

The results are shown in Table 13. The conversion and selectivity for each 15 min segment of the run are shown. The highest selectivity was achieved during the 45–60 min segment when the temperature was 150° C. and a flow rate of 400 sccm of 25% oxygen was employed. Lower selectivities were achieved at the lower temperature (125° C.) and higher oxygen concentration.

TABLE 13

Oxidation of 25% NMG over Pt/Attrited PVP

| Interval (min.) | Temp. (° C.) | $O_2$ mole fraction (%) | Incremental Conversion (%) | Incremental Selectivity (%) |
|---|---|---|---|---|
| 0–15 | 125 | 25 | 10.2 | — |
| 15–30 | 125 | 25 | 8.9 | 86.7 |
| 30–45 | heating | 25 | 9.0 | 81.8 |
| 45–60 | 150 | 25 | 6.1 | 96.5 |
| 60–75 | 150 | 37.5 | 8.8 | 80.8 |
| 75–90 | 150 | 37.5 | 7.9 | 71.9 |

Example 22

This example describes the preparation of Pt on PVP catalysts using a method involving pre-treatment of the PVP resin with an acid or mixture of acids followed by neutralization and reduction in non-aqueous solvents, typically alcohols. The purpose of the acid pre-treatment is to improve the dispersion of Pt by causing the Pt to deposit primarily in the interior of the polymer bead rather than the outer surface. The acid preferably is neutralized before reduction so that it does not destroy the $NaBH_4$ reducing agent. The use of non-aqueous solvents is preferred for this step because treatment of PVP impregnated with $H_2PtCl_6$ with aqueous base leads to leaching of most the Pt from the resin. This does not occur when ethanol, methanol, or similar solvents are used instead.

In this example, Reillex HP PVP, having a moisture content of 69.3 wt %, was used as received from Reilly Industries (Indianapolis, Ind.). Six 32.6 g samples of the wet resin (10.0 g dry weight) were combined with 100 ml of water in separate round-bottom flasks equipped with stir bars. Approximately 0.105 moles of acid were added to each of the suspensions. The acids used are shown in Table 14.

TABLE 14

Acids Used to Pre-Treat the PVP Resin

| Sample Number | Acids Used | Proportion of Acid (mole %) | Mass of Acid (g) |
|---|---|---|---|
| 1 | Acetic Acid | 100 | 6.31 |
| 2 | Trifluoroacetic Acid | 100 | 11.97 |
| 3 | Nitric acid (70% in $H_2O$) | 100 | 6.62 |
| 4 | Acetic acid | 25 | 1.58 |
|   | Trifluoroacetic Acid | 75 | 8.58 |
| 5 | Acetic Acid | 50 | 3.15 |
|   | Trifluoroacetic Acid | 50 | 5.99 |
| 6 | Acetic Acid | 75 | 4.73 |
|   | Trifluoroacetic Acid | 25 | 2.99 |

Approximately 1.35 g of $H_2PtCl_6$ (Aldrich Chemical, Milwaukee, Wis.) was added after the acid resin mixture had been stirred for 80 min. After 1 hr of stirring, the platinized resin was recovered by filtration, washed three times with 150 ml of water, and dried under vacuum at 120° C. for 68 hr. Each sample then was suspended in 100 ml of a mixture formed by mixing 136 g of 25 wt % sodium methoxide in methanol with 450 ml of methanol. After stirring the suspension for 1 min, 6.5 g of 12 wt % $NaBH_4$ in 14 molar NaOH was added. The suspensions were stirred for 90 min., and then allowed to sit for 16 hr. The solid was recovered by filtration, washed 3 times with 150 ml of water, and dried overnight under vacuum at 120° C.

The relative amounts of Pt on the surface and interior of the beads were qualitatively determined by optical microscopy. It was apparent using this method that catalysts 2 and 3 (treated with trifluoroacetic and nitric acid, respectively)

had Pt deposited deep in the interior. Deeper penetration was observed where nitric acid (a stronger acid) (catalyst 3) was used. Catalysts 1 and 4–6, which used acetic acid and mixtures of acetic acid with stronger acid, had Pt deposition mostly near, but not on, the surface of the bead.

The activity and selectivity of the catalysts for NMG oxidation was determined under the reaction conditions of Example 8. Table 15 shows the results. In general, the conversions of the catalysts pre-treated with acid are poor compared to catalysts not pre-treated with acid, see, e.g., Examples 20 and 21. This suggests that catalysts having the Pt primarily in the interior of the PVP bead are less active for N-substituted glyphosate oxidation than catalysts in which the Pt is mostly on the bead surface. A more detailed examination of the data further reveals that the use of stronger acid, which leads to deposition of the platinum deeper in the particle, tends to lead to progressively less active and less selective catalysts. Thus, the preferred Pt on PVP catalysts for the oxidation of N-glyphosates substituted glyphosates are those in which the Pt is primarily deposited onto the surface of the support.

TABLE 15

Conversion and selectivity of catalysts prepared using acid pretreatment

| Sample No. | Acids Used* | Conv. (%) | Selectivity (%) | | |
|---|---|---|---|---|---|
| | | | Glyphosate | (M)AMPA | $H_3PO_4$ |
| 1 | Acetic | 19.3 | 86.8 | 11.2 | 2.0 |
| 2 | TFA | 8.8 | 69.7 | 22.4 | 7.9 |
| 3 | Nitric acid | 3.7 | 45.8 | 44.0 | 10.2 |
| 4 | 3:1 TFA:Acetic | 12.3 | 60.2 | 34.8 | 5.0 |
| 5 | 1:1 TFA:Acetic | 10.5 | 72.4 | 22.6 | 5.0 |
| 6 | 1:3 TFA:Acetic | 11.2 | 63.4 | 31.2 | 5.4 |

*TFA = trifluoroacetic acid

Example 23

This example describes the preparation of a Pt catalyst supported on a different polymer support, sulfonated polystyrene. The resin is sulfonated to convert it to a cation exchange resin, and a base metal (preferably iron) is deposited and reduced to serve and as in situ reducing agent for Pt. A specific preparation procedure follows.

A. Sulfonation

The following steps were conducted in a fume hood, due to the fact that $SO_3$ is evolved during this process.

Approximately 20 g of a polystyrene resin (Amberlite XAD-16, Sigma Chemical, St. Louis, Mo.) was placed into a beaker. The resin was sulfonated by slowly adding chlorosulfonic acid to the resin by pipet. Small amounts were added in a step-wise fashion because the reaction is vigorous. Enough chlorosulfonic acid was added to barely cover the resin, so that a paste-like consistency resulted. The resin was allowed to stand in the chlorosulfonic acid for approximately 2 hr, with occasional stirring with a spatula. The resin turned black during this procedure. In a separate beaker, approximately 300 ml of a cold saturated solution of sodium sulfate was prepared, and a few ml of concentrated sulfuric acid were added to it. The resin was then poured into the sodium sulfate solution. Afterward, the resin was filtered and rinsed on a glass frit with saturated sodium sulfate solution. Finally the resin was rinsed with deionized water and dried in a vacuum oven at 100° C.

B. Base Metal Treatment

This procedure preferably is performed as rapidly as possible or under an inert atmosphere, because the iron on the resin is relatively unstable in air.

Approximately 1.01 g of dry sulfonated XAD-16 resin and 60 ml of water were combined in a beaker on a stir plate. Ferric chloride in excess (3–4 g) was added to the solution while stirring. The resin then was filtered and washed on a glass frit with deionized water. The resin was returned to a beaker, more deionized water was added, and $NaBH_4$ was added to reduce the iron. The resin was filtered on a glass frit and returned to the beaker so that more water could be added.

C. Depositing Pt on the Resin

The XAD-16 was re-suspended in 60 ml of water, and 0.32 g of $H_2PtCl_6$ dissolved in 30 ml of water was added. The amount of $H_2PtCl_6$ was based on the weight of the resin and the desired Pt content of the final catalyst. This solution was added in several portions to the base metal resin while stirring. After stirring for approximately 20 min, the resin was filtered and rinsed on a glass frit with deionized water. The resin was then reduced with $NaBH_4$. After the Pt was reduced, the catalyst was washed several times with 10–30% sulfuric acid to remove residual iron. The catalyst was filtered and rinsed with deionized water and then dried in a vacuum oven at 100° C. This made a catalyst containing about 10% Pt.

D. Catalyst Performance

Approximately 100 mg of catalyst was used to effect the oxidation of 1.0 g of NMG in 20 ml of water to form glyphosate. Each run was conducted for approximately 5 hr in a 50 ml round-bottom flask equipped a water-cooled reflux condenser. Oxygen was bubbled through the reaction mixture for the entire 5 hr at reflux. At the completion of each run, the reaction mixture was filtered to remove the catalyst. For comparison purposes, approximately 100 mg of the sulfonated and un-sulfonated resin were also tested under the same reaction conditions.

The results are shown in Table 16. The resins without Pt were inactive, and the selectivity of the Pt on sulfonated resin was similar to that of platinum black and Pt on PVP.

The results are shown in Table 16. The resins without Pt were inactive, and the selectivity of the Pt on sulfonated resins was similar to that of platinum black

TABLE 16

Use of a Polystyrene Resin Supported Catalysts to Oxidize NMG to Glyphosate

| Catalyst | Conv. (%) | Glyphosate Select. (%) | (M)AMPA Select. (%) | $H_3PO_4$ Select. (%) |
|---|---|---|---|---|
| XAD-16 untreated | <2 | — | — | — |
| Sulfonated XAD-16 | <2 | — | — | — |
| 10% Pt/sulfonated XAD-16 | 9.2 | 82.7 | 3.4 | 13.9 |

Example 24

This example demonstrates the preparation and use of a platinum catalyst on an acidic hydrophilic polymer bead support (i.e., $H^+$ form sulfonated cross-linked polystyrene).

Approximately 20 g of H+ form sulfonated polystyrene beads (Amberlyst 15, Rohm & Haas, Philadelphia, Pa.) was combined with a solution containing 2.7 g of $H_2PtCl_6$ (37.5% Pt, equivalent to 1.0 g of Pt, Aldrich Chemical, Milwaukee, Wis.) in 120 ml of absolute ethanol and 80 ml of water. The solution was refluxed while stirring in a 95° C. oil bath for 40 hr. Afterwards, the resin was black and the solution was clear. The catalyst was recovered by filtration; rinsed with water; and soaked, unstirred for 1 hr in 200 g of 20% $Na_2SO_4$ to de-protonate the —$SO_3H$ groups. The catalyst was again recovered by filtration and washed with water, but not dried.

Subsequently, the catalyst was used to oxidize NMG to form N-(phosphonomethyl)glycine. To conduct the oxidation, the catalyst was placed into the 300 ml autoclave reactor described in Example 17, along with 105.4 ml of water and 47.1 g of NMG. The reaction was conducted at a temperature of 135° C., a pressure of 66 psig, and an oxygen flow rate of 100 sccm for 2 hr. Table 17 shows the selectivities and conversions achieved.

TABLE 17

Oxidation of NMG Using Platinum on H+ Form Sulfonated Polystyrene Beads

| Time (min.) | Conversion (%) | Selectivity (%)* | | |
|---|---|---|---|---|
| | | glyphosate | (M)AMPA | $H_3PO_4$ |
| 30 | 14.8 | 93.5 | 2.1 | 4.4 |
| 60 | 29.3 | 92.0 | 2.4 | 5.6 |
| 90 | 40.8 | 87.2 | 4.4 | 8.4 |
| 120 | 50.6 | 81.2 | 8.4 | 9.5 |

*Incremental selectivities

Example 25

This example describes the preparation and use of Pt catalysts in conjunction with inorganic modifiers (also referred to as "promoters"). In this example, a variety of metal compounds (mostly metal halides) were used to modify platinum black. The platinum black and all of the metal compounds were obtained from Aldrich Chemical Co., Milwaukee, Wis. The metal compounds tested are listed in table 18 below.

Because all the metal compounds are moisture sensitive, all manipulations other than hydrolysis were performed in a dry glove box under a $N_2$ atmosphere. Separate portions of platinum black (0.15–0.25 g) were placed into 40 ml vials with Teflon faced septa outside of the glove box. Each portion was designated as to which metal compound would be used for treatment. All materials were transferred into the dry glove box, taking care to remove air before actual glove box procedures. A small amount of the metal compound (approximately 1 g) was placed into its designated 40 ml vial in the glove box. Chlorobenzene (approximately 40 ml) was added to each metal compound. Each vial was capped and mixed to effect dissolution. All these solutions were saturated, as evidenced by solid metal compound remaining on the bottom of the vials. The metal compound solutions (3–5 ml) were poured into the designated vials containing platinum black, taking care not to add the metal compound which had not dissolved. Each vial containing platinum black was capped and mixed by shaking in the glove box. The vials were then uncapped and allowed to stand for 1 hr inside the glove box. The vials containing platinum black were then capped and removed from the glove box and placed into a hood. Deionized water (approximately 20 ml) was carefully added to each vial to hydrolyze the metal compound salts. Each catalyst then was filtered on a glass frit filter, washed with copious amounts of water, and dried under vacuum overnight.

Approximately 30 mg of each of the catalysts so prepared were used to effect the oxidation of 1.0 g of NMG in 20 ml of water to form glyphosate. Each run was conducted for approximately 5 hr in a 50 ml round-bottom flask equipped a water-cooled reflux condenser. Oxygen was bubbled through the reaction mixture for the entire 5 hr at reflux. At the completion of each run, the reaction mixture was filtered to remove the catalyst. For comparison purposes, a control sample of unmodified platinum black also was used to effect the NMG oxidation under the same conditions.

Table 18 lists the metal compounds tested and their effects on selectivity. Compounds of gallium, indium, ruthenium, and osmium were effective in raising selectivity.

TABLE 18

Screening of Platinum Black Catalysts Treated with Metal Compounds

| Metal Compound | Conv. (%) | Selectivity to (%) | | |
|---|---|---|---|---|
| | | Glyphosate | (M)AMPA | $H_3PO_4$ |
| None | 34.2 | 85.5 | 4.5 | 10.0 |
| $InBr_3$ | 33.0 | 94.3 | 2.1 | 3.6 |
| $RuBr_3$ | 45.8 | 91.9 | 1.3 | 6.7 |
| $OsO_4$ | 47.5 | 90.4 | 2.1 | 7.6 |
| $GaBr_3$ | 10.4 | 90.0 | 2.6 | 7.4 |
| $SbBr_3$ | 38.5 | 84.7 | 1.5 | 13.8 |
| $TaBr_5$ | 44.5 | 84.4 | 2.2 | 13.4 |
| $SnBr_4$ | 32.0 | 70.5 | 4.6 | 24.8 |
| $MnCl_2$ | 27.5 | 70.0 | 9.0 | 21.0 |
| $RhBr_3$ | 20.3 | 68.6 | 6.0 | 25.4 |
| $FeCl_3$ | 23.7 | 56.0 | 15.4 | 28.6 |
| $BiBr_3$ | 5.2 | 40.2 | 13.5 | 46.3 |
| $(NH_4)_2WO_4$ | 28.0 | 38.1 | 9.6 | 52.3 |
| $Ce(OH)_4$ | 57.6 | 20.4 | 5.9 | 73.7 |

Example 26

This example illustrates the influence of stirring rate on selectivity in the oxidation of N-substituted glyphosates at greater temperatures and oxidation rates.

In each of 3 runs, approximately 4.501 g of catalyst was combined with 116.6 g of water, 40.06 g of NMG, and 0.65 ml of a 0.041 g/ml solution of TEMPO in acetonitrile in a 300 ml stirred autoclave equipped with fritted tubes for gas introduction and liquid withdrawal. The liquid withdrawal frit was located below the stirrer, and the gas introduction frit was above and to the side of the stirrer. The reactor was closed and pressurized to 85 psig with nitrogen and heated to 125° C.

Tables 19, 20, and 21 below give the stirrer rate at each interval in the three runs, as well as the selectivity and average oxidation rate achieved during the interval. Both rate and selectivity are seen to improve with stir rate up to a clear optimum of 1000 rpm. The reported rate is expressed in terms of moles of NMG oxidized per liter per hour. When the stirring was increased to 1200 rpm during the second run, the selectivity decreased. The 1200 rpm selectivity was even worse at the beginning of the third run.

In the reactor described, the degree to which gas is pulled down into the vortex created by the impeller and prevented from bubbling, un-reacted, to the surface increases with the stirring rate up to about 950 rpm, at which point virtually all the gas is pulled into the turbulent zone around the impeller. As the stir rate increases further, however, the turbulent zone of gas-liquid mixing around the impeller widens until, at about 1500 rpm, it fills most of the liquid volume. The data below demonstrates that the optimal stirrer speed for the aerobic oxidation of NMG is that which is just sufficient to substantially prevent the gas bubbles from rising directly to the upper surface of the solution upon their introduction into the solution. Stirrer speeds significantly less than this preferred value tend to cause lower reaction rates and selectivities, while stirrer speeds significantly greater than the preferred value tend to create a wider zone of turbulence which also tends to cause a lower selectivity.

TABLE 19

Effect of Stirring Rate on NMG Oxidation, Run 1

| Interval (min.) | Stir rate (rpm) | Rate (mol/L-hr) | Glyphosate Selectivity (%) |
|---|---|---|---|
| 0–60 | 200 | 0.10 | 81.8 |
| 60–120 | 400 | 0.30 | 81.4 |
| 120–210 | 600 | 0.48 | 88.0 |

TABLE 20

Effect of Stirring Rate on NMG Oxidation, Run 2

| Interval (min.) | Stir rate (rpm) | Rate (mol/L-hr) | Glyphosate Selectivity (%) |
|---|---|---|---|
| 0–30 | 600 | 0.31 | 90.0 |
| 30–60 | 800 | 0.47 | 94.0 |
| 60–90 | 1000 | 0.75 | 95.4 |
| 90–105 | 1200 | 0.47 | 93.8 |

TABLE 21

Effect of stirring rate on NMG oxidation, Run 3

| Interval (min.) | Stir rate (rpm) | Rate (mol/L-hr) | Glyphosate Selectivity (%) |
|---|---|---|---|
| 0–15 | 1200 | 0.67 | 78.7 |
| 15–30 | 1400 | 0.63 | 81.8 |
| 30–45 | 1600 | 0.74 | 82.9 |
| 45–60 | 1800 | 0.75 | 83.4 |

Example 27

This example illustrates various methods that have been used in accordance with this invention to reduce the adverse effect of undissolved oxygen in the reaction solution.

Three runs were conducted. In each, NMG was oxidized to N-(phosphonomethyl)glycine using a platinum black (Aldrich Chemical Co., Milwaukee, Wis.) catalyst. This reaction was conducted in the stirred reactor used in Example 17 with a stir rate of 1000 rpm.

In the first run, the platinum black catalyst was modified by depositing N,N'-bis-(3-methylphenyl)-N,N'-diphenyl benzidine ("TPD") onto the surface of the catalyst. This catalyst was prepared by suspending 0.70 g of platinum black in 20 ml of methylene chloride containing 7 mg of dissolved TPD. The catalyst was introduced into the reactor along with 40.1 g of NMG and 113 g of water. The pressure was maintained at 90 psig. Approximately 200 sccm of oxygen were bubbled through the mixture once the solution reached the reaction temperature (150° C.). After 32 min., the conversion was 60.4% and the selectivity was 90.8%. After 56 min., the conversion was 77.2% and the selectivity was 83.1%.

In the second run, the reactor was loaded with 0.70 g. of platinum black, 40.0 g of NMG, and 113.3 g of water. The pressure was maintained at 90 psig. The reactor used in Example 17 was modified so that oxygen was introduced through a frit which was placed near the surface of the reaction solution (i.e., about 1.3 cm from the surface in a reaction mixture having a total depth of about 15.2 cm) so that essentially all the oxygen bubbles could escape into the headspace without first coming into contact with the impeller (before this modification, the location of the frit was lower in the reaction mixture, thereby allowing a significant amount of oxygen bubbles to come into contact with the impeller). Approximately 200 sccm of oxygen were bubbled through the mixture once the solution reached the reaction temperature (150° C.). After 30 min, the conversion was 59.6% and the selectivity was 92.0%. After 60 min, the conversion was 80.5% and the selectivity was 81.8%.

In the third run, 47.2 g of NMG, 103.7 ml of water, and 2.00 g of platinum black were loaded into the reactor using the same frit position as in the third run. The pressure was maintained at 66 psig. When the solution reached the reaction temperature (135° C.), oxygen was bubbled into the solution at a flow rate of 100 sccm. Table 22 shows the conversion and incremental selectivity during the reaction.

TABLE 22

Oxidation of NMG Using a Frit Positioned Away From Impeller

| Time (min.) | Conversion (%) | Selectivity (%)* | | |
|---|---|---|---|---|
| | | glyphosate | (M)AMPA | $H_3PO_4$ |
| 18 | 15.7 | 94.9 | 1.2 | 3.9 |
| 36 | 31.7 | 97.3 | 0.3 | 2.3 |
| 55 | 49.6 | 93.6 | 1.0 | 5.4 |
| 72 | 66.0 | 96.1 | 1.1 | 2.8 |
| 90 | 83.3 | 92.3 | 2.2 | 5.5 |

*Incremental selectivities

Example 28

This example describes the reductive coupling of monoethanolamine with acetone to form N-isopropyl monoethanolamine (abbreviated "IMEA").

A series of runs were conducted utilizing various Pt-containing and Pd-containing catalysts. In each run, the catalyst was suspended in 25 ml of acetone in a glass pressure bottle equipped with a stir bar. Approximately 6.1 g (0.1 mole) of monoethanolamine was then added to the pressure bottle, and the mixture was stirred and allowed to stand for 5–10 min. A small amount of heat was evolved. The bottle was then pressurized to 90 psig with $H_2$, and stirred overnight at room temperature at the same pressure. Subsequently, the bottle was de-pressurized, and the relative proportions of monoethanolamlne, N-isopropyl monoethanolamine, and N,N-diisopropyl ethanolamine were determined by gas chromatography.

The catalysts shown in Table 23 were found to be the preferred catalysts for the reaction. Although rhodium on carbon (not shown in Table 23) was found to promote the reductive alkylation of acetone and monoethanolamine, it gave primarily the di-alkylated product. Raney nickel (also not shown in Table 23) exhibited low activity for the desired reaction (<40% conversion using 0.205 g. of 5% Rh/C).

Without being bound by any particular theory, it is believed that the acetone derivatives quantified in Table 23 are a result of the aldol condensation, as shown by the following equation:

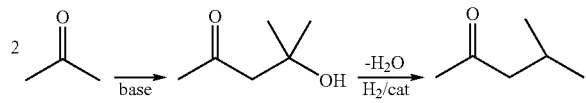

In addition to showing the preferred catalysts for the reaction, this example also demonstrates that acetone may be used as both solvent and reagent, eliminating the need to use ethanol or any other non-reactive solvent (i.e., any solvent which is non-reactive with the reactants and the desired product under the reaction conditions) under traditional protocols.

TABLE 23

Room temperature reductive alkylations of Monoethanolamine with acetone at 90 psi $H_2$

| Catalyst | Catalyst Loading (g) | IMEA (%) | Diisopropyl MEA (%) | % Acetone Derivatives |
|---|---|---|---|---|
| 5% Pt/SiO$_2$ | .262 | 96 | 0.1 | 0.9 |
| 53% Pd on carbon (1% H$_2$SO$_4$ in the acetone) | .438 | 78.8 | 0.2 | 20 |
| 10% Pt on NCP-14 carbon | .301 | 90.1 | 2.1 | 7.3 |
| 5% Pd on carbon | .310 | 81.7 | 0.1 | 13.4 |
| Palladium hydroxide | 91.7 | 73.3 | ND | 14.3 |
| Palladium oxide | .0373 | 27 | ND | 13.6 |
| No catalyst | — | 1 | ND | 42.2 |

Example 29

This example demonstrates the neutralization of sodium sarcosinate mediated by ion exchange membranes. The neutralization was conducted in an apparatus composed of two glass pieces. The lower piece was bowl-shaped except for a flange at the top with a groove inscribed for a 44 mm O-ring. The upper piece was cylindrical with a flange on the bottom identical to that on the lower piece. During operation, a Viton O-ring was placed in the upper flange and a piece of the membrane was sandwiched between the flange on the lower piece and the O-ring. The two pieces were held tightly together with a clamp.

To prepare the apparatus for use, the lower piece of the apparatus was filled with a phosphonomethylation mixture (27 ml) prepared by combining 37.5 g (0.205 moles) of NMG, 20.9 g of concentrated sulfuric acid (1.0 equiv.), 16.6 g of 37% formalin (0.20 equiv.), and 212.3 g of water. This yielded a 15% NMG solution containing amounts of sulfuric acid and formalin which are typical of phosphonomethylation mixtures.

After the lower piece was completely filled with the phosphonomethylation mixture, the membrane was placed on top before assembling the apparatus. Care was taken to avoid bubbles between the phosphonomethylation mixture and the membrane. Once the apparatus was assembled, 50 ml of a 5% aqueous solution of sodium sarcosinate was added to the upper (cylindrical) piece. A pH probe was inserted into the sodium sarcosinate solution, and magnetic stirring of the two solutions was initiated. The pH of the upper solution decreased as the neutralization proceeded.

The following membranes were tested using the above equipment and protocol: Nafion 117 (manufactured by DuPont Co. of Wilmington, Del. and available from Aldrich Chemical of Milwaukee, Wis.); Ionclad EDS R4010 membrane (Pall Specialty Materials of Port Washington, N.Y.); and Raipore R1010, Ionac, and ESC 7000 membranes (available from The Electrosynthesis Company of East Amherst, N.Y.). All the membranes were effective in mediating the neutralization. The R4010 membrane was the fastest and exhibited proton fluxes of 0.03 amperes per square centimeter.

Example 30

This example demonstrates the use of nanofiltration membranes to remove bisulfate ions from a simulant also containing NMG, glyphosate, and dihydrogen phosphate. The proportions of these components in the simulant are representative of those in processes in which an N-substituted glyphosate is prepared by phosphonomethylation catalyzed by $H_2SO_4$, and then oxidized to glyphosate after neutralization of the $H_2SO_4$ without first isolating the N-substituted glyphosate as a solid. The example suggests that molecular weight cutoffs below 1000 daltons are preferred for this application.

The composition of the simulant was 1.0% NMG, 0.2% glyphosate, 2.7% $NaHSO_4.H_2O$, and 0.3% $NaH_2PO_4.H_2O$ in water (pH=1.4). The mixture was homogeneous at room temperature. Approximately 100 ml of the simulant was charged to a SepaST stirred membrane test cell (Osmonics Laboratory and Specialty Products Group, Livermore, Calif.). The cell held a 45 mm disk of the membrane being tested. Helium pressure was applied to the chamber holding the simulant and the permeate was collected and analyzed for NMG, glyphosate, and phosphate concentration by HPLC and for sulfate content by ion chromatography.

Table 24 shows the results for two types of low molecular weight cutoff nanofiltration membranes. The first set are Nova 1k, 3k, and 5k membranes (Pall Gelman, Ann Arbor, Mich.). These membranes are characterized by their manufacturer as possessing molecular weight cutoffs of 1000, 3000 and 5000 daltons, respectively. The other set are two SelRO membranes, MPF-34 and MPF-36 (LCI Corporation, Charlotte, N.C.). The manufacturer does not specify a molecular weight cutoff, but the membranes exhibit 95% and 50% rejection of sucrose (molecular weight=342), respectively. Thus, the order of molecular weight cutoff is Nova 5k>Nova 3k>Nova 1k>SelRO MPF-36>SelRO MPF-34.

Table 24 shows the rejection efficiencies for NMG and glyphosate and the relative selectivity of the membrane for sulfate and phosphate with respect to NMG. A selectivity value of 1.0 means that the membrane is not selective. The SelRO membranes exhibit selectivities significantly greater than 1.0, and are therefore effective for this application.

TABLE 24

Membrane Selectivity for Separation of Sulfate and Phosphate from NMG and Glyphosate

| Membrane | Pressure (psi) | Rejection NMG | Efficiency Glyphosate | Relative SO$_4$/ NMG | Selectivity PO$_4$/NMG |
|---|---|---|---|---|---|
| Nova 5k | 70 | 0.05 | 0.05 | 1.02 | 1.01 |
| Nova 3k | 100 | 0.05 | 0.05 | 0.99 | 1.00 |

TABLE 24-continued

Membrane Selectivity for Separation
of Sulfate and Phosphate from NMG and Glyphosate

| Membrane | Pressure (psi) | Rejection NMG | Efficiency Glyphosate | Relative $SO_4$/NMG | Selectivity $PO_4$/NMG |
|---|---|---|---|---|---|
| Nova 1k | 100 | 0.10 | 0.10 | 1.05 | 1.04 |
| SelRO MPF-36 | 440 | 0.93 | 0.80 | 4.87 | 1.03 |
| SelRO MPF-34 | 440 | 0.93 | 0.99 | 4.63 | 1.49 |

The above description of the preferred embodiment is intended only to acquaint others skilled in the art with the invention, its principles, and its practical application, so that others skilled in the art may adapt and apply the invention in its numerous forms, as may be best suited to the requirements of a particular use. The present invention, therefore, is not limited to the above embodiments and may be variously modified.

We claim:

1. An oxidation catalyst comprising a noble metal, an electroactive molecular species having an oxidation potential of at least about 0.3 volts vs. SCE and a support comprising a polymer, wherein the noble metal is on the support.

2. The oxidation catalyst of claim 1 wherein the electroactive molecular species is hydrophobic.

3. The oxidation catalyst of claim 1 wherein the electroactive molecular species comprises a compound selected from the group consisting of triphenylmethane; N-hydroxyphthalimide; 2,4,7-trichlorofluorene; N,N'-bis(3-methylphenyl)-N,N'-diphenyl benzidine; tris(4-bromophenyl) amine; 2,2,6,6-tetramethyl piperidine N-oxide; 5,10,15,20-tetraphenyl-21H,23H-porphine iron(III) chloride; 5,10,15,20-tetraphenyl-21H,23H porphine nickel(II); 4,4'-difluorobenzophenone; 5,10,15,20-tetrakis (pentafluorophenyl)-21H,23H-porphine iron (III) chloride; and phenothiazine.

4. The oxidation catalyst of claim 1 wherein the electroactive molecular species comprises 2,2,6,6-tetramethyl piperidine N-oxide.

5. The oxidation catalyst of claim 1 wherein the electroactive molecular species comprises a triarylamine.

6. The oxidation catalyst of claim 1 wherein the electroactive molecular species comprises N,N'-bis(3-methylphenyl)-N,N'-diphenyl benzidine.

7. The oxidation catalyst of claim 1 wherein (a) the catalyst comprises a promoter, and (b) at least about 0.05% by weight of the catalyst consists of the promoter.

8. The oxidation catalyst of claim 7 wherein the promoter comprises a metal selected from the group consisting of aluminum, ruthenium, osmium, indium, gallium, tantalum, tin, and antimony.

9. The oxidation catalyst of claim 1 wherein the support comprises a polymer selected from the group consisting of polyamide, polyimide, polycarbonate, polyurea, and polyester.

10. The oxidation catalyst of claim 1 wherein the support comprises a polymer selected from the group consisting of polyethylene imine, polyaminostyrene, sulfonated polystyrene, polyvinyl pyridine, and a salt of polyacrylic acid.

11. The oxidation catalyst of claim 1 wherein the support comprises polystyrene.

12. The oxidation catalyst of claim 1 wherein the support comprises polystyrene substituted with dimethylamine groups.

13. The oxidation catalyst of claim 1 wherein the support comprises sulfonated polystyrene.

14. The oxidation catalyst of claim 1 wherein the support comprises polyvinyl pyridine.

15. The oxidation catalyst of claim 1 wherein the electroactive molecular species comprises a compound selected from the group consisting of N-hydroxyphthalimide; 2,2,6,6-tetramethyl piperidine N-oxide; N,N'-bis(3-methylphenyl)-N,N'-diphenyl benzidine; and tris(4-bromophenyl) amine.

16. The oxidation catalyst of claim 1 wherein the electroactive molecular species is on the surface of the noble metal.

17. The oxidation catalyst of claim 9 wherein the electroactive molecular species is on the surface of the noble metal, the surface of the support or both.

18. The oxidation catalyst of claim 1 wherein the catalyst comprises a noble metal selected from the group consisting of platinum, palladium, rhodium, iridium, osmium and gold.

19. The oxidation catalyst of claim 1 wherein the catalyst comprises platinum.

20. The oxidation catalyst of claim 1 wherein the support is in the form of cross-linked beads.

21. The oxidation catalyst of claim 20 wherein the cross-linked beads are porous.

22. The oxidation catalyst of claim 20 wherein the cross-linked beads have a surface area of at least about 10 m2/g.

23. The oxidation catalyst of claim 1 wherein the polymer is capable of being protonated by an acidic noble metal compound.

24. An oxidation catalyst comprising a noble metal and an electroactive molecular species comprising a compound selected from the group consisting of triphenylmethane; N-hydroxyphthalimide; 2,4,7-trichlorofluorene; N,N'-bis (3-methylphenyl) -N,N'-diphenyl benzidine; tris (4- bromophenyl)amine; 2,2,6, 6-tetramethyl piperidine N-oxide; 4,4'-difluorobenzophenone; 5,10, 15,20-tetrakis (pentafluorophenyl) - 21H,23H-porphine iron (III) chloride; and phenothiazine.

25. The oxidation catalyst of claim 24 wherein the electroactive molecular species comprises 2,2,6, 6-tetramethyl piperidine N-oxide.

26. The oxidation catalyst of claim 24 wherein the electroactive molecular species comprises a triarylamine.

27. The oxidation catalyst of claim 24 wherein the electroactive molecular species comprises N,N'-bis (3- methylphenyl)-N,N'-diphenyl benzidine.

28. The oxidation catalyst of claim 24 wherein (a) the catalyst comprises a promoter, and (b) at least about 0.05% by weight of the catalyst consists of the promoter.

29. The oxidation catalyst of claim 28 wherein the promoter comprises a metal selected from the group consisting of aluminum, ruthenium, osmium, indium, gallium, tantalum, tin, and antimony.

30. The oxidation catalyst of claim 24 wherein the catalyst comprises a support comprising a material selected from the group consisting of carbon, alumina, silica, titania, zirconia, siloxane, and barium sulfate and wherein the noble metal is on the support.

31. The oxidation catalyst of claim 30 wherein the support comprises a material selected from the group consisting of alumina, silica, titania, zirconia, siloxane, and barium sulfate.

32. The oxidation catalyst of claim 30 wherein the support comprises a material selected from the group consisting of silica, titania, and barium sulfate.

33. The oxidation catalyst of claim 30 wherein the support comprises graphitic carbon.

34. The oxidation catalyst of claim 24 wherein the catalyst comprises a support comprising a polymer and the noble metal is on the support.

35. The oxidation catalyst of claim 34 wherein the support comprises a polymer selected from the group consisting of polyamide, polyimide, polycarbonate, polyurea, and polyester.

36. The oxidation catalyst of claim 34 wherein the support comprises a polymer selected from the group consisting of polyethylene imine, polyaminostyrene, sulfonated polystyrene, polyvinyl pyridine, and a salt of polyacrylic acid.

37. The oxidation catalyst of claim 34 wherein the support comprises polystyrene.

38. The oxidation catalyst of claim 34 wherein the support comprises polystyrene substituted with dimethylamine groups.

39. The oxidation catalyst of claim 34 wherein the support comprises sulfonated polystyrene.

40. The oxidation catalyst of claim 34 wherein the support comprises polyvinyl pyridine.

41. The oxidation catalyst of claim 34 wherein the support is in the form of cross-linked beads.

42. The oxidation catalyst of claim 41 wherein the cross-linked beads are porous.

43. The oxidation catalyst of claim 41 wherein the cross-linked beads have a surface area of at least about 10 m2/g.

44. The oxidation catalyst of claim 34 wherein the polymer is capable of being protonated by an acidic noble metal compound.

45. The oxidation catalyst of claim 24 wherein the electroactive molecular species comprises a compound selected from the group consisting of N-hydroxyphthalimide; 2,2,6,6- tetramethyl piperidine N-oxide; N,N'-bis (3-methylphenyl) -N,N'- diphenyl benzidine; and tris (4-bromophenyl) amine.

46. The oxidation catalyst of claim 24 wherein the electroactive molecular species is on the surface of the noble metal.

47. The oxidation catalyst of claim 34 wherein the electroactive molecular species is on the surface of the noble metal, the surface of the support or both.

48. The oxidation catalyst of claim 24 wherein the catalyst comprises a noble metal selected from the group consisting of platinum, palladium, rhodium, iridium, osmium and gold.

49. The oxidation catalyst of claim 24 wherein the catalyst comprises platinum.

50. An oxidation catalyst comprising a noble metal, an electroactive molecular species having an oxidation potential of at least about 0.3 volts vs. SCE and a support comprising a material selected from the group consisting of alumina, silica, titania, zirconia, siloxane, and barium sulfate and wherein the noble metal is on the support.

* * * * *

UNITED STATES PATENT AND TRADEMARK OFFICE
CERTIFICATE OF CORRECTION

| | | |
|---|---|---|
| PATENT NO. | : 7,297,657 B2 | Page 1 of 1 |
| APPLICATION NO. | : 10/441454 | |
| DATED | : November 20, 2007 | |
| INVENTOR(S) | : Morgenstern | |

It is certified that error appears in the above-identified patent and that said Letters Patent is hereby corrected as shown below:

Column 8, line 38: "$R^3$, $R^4$, and $R^1$" should read -- $R^3$, $R^4$, and $R^5$ --.

Column 16, lines 3-4: "hydrocarbyl-other" should read -- hydrocarbyl other --.

Column 19, line 13: "-$PO_3R^2R^{13}$," should read -- -$PO_3R^{12}R^{13}$, --.

Column 19, line 15: "$R^2$," should read -- $R^{12}$, --.

Column 32, line 64: "Boreskov institute" should read -- Boreskov Institute --.

Column 45, line 19: "N-glyphosates substituted" should read -- N-substituted --.

Column 46, line 46: "The results are shown in Table 16. The resins without Pt were inactive, and the selectivity of the Pt on sulfonated resins was similar to that of platinum black" should be deleted.

Column 54, claim 17, line 12: "claim 9" should read -- claim 1 --.

Signed and Sealed this

Sixteenth Day of September, 2008

JON W. DUDAS
*Director of the United States Patent and Trademark Office*